(12) United States Patent
Ortyn et al.

(10) Patent No.: US 6,875,973 B2
(45) Date of Patent: Apr. 5, 2005

(54) AUTO FOCUS FOR A FLOW IMAGING SYSTEM

(75) Inventors: William E. Ortyn, Bainbridge Island, WA (US); Michael J. Seo, Mercer Island, WA (US); David A. Basiji, Seattle, WA (US); Keith L. Frost, Seattle, WA (US); David J. Perry, Woodinville, WA (US)

(73) Assignee: Amnis Corporation, Seattle, WA (US)

( * ) Notice: Subject to any disclaimer, the term of this patent is extended or adjusted under 35 U.S.C. 154(b) by 0 days.

(21) Appl. No.: 10/822,170

(22) Filed: Apr. 9, 2004

(65) Prior Publication Data

US 2004/0217256 A1 Nov. 4, 2004

Related U.S. Application Data

(63) Continuation-in-part of application No. 10/348,193, filed on Jan. 16, 2003, now Pat. No. 6,778,263, which is a continuation-in-part of application No. 09/939,292, filed on Aug. 24, 2001, now Pat. No. 6,532,061.
(60) Provisional application No. 60/462,574, filed on Apr. 11, 2003, and provisional application No. 60/228,076, filed on Aug. 25, 2000.

(51) Int. Cl.$^7$ .............................................. G02B 27/40
(52) U.S. Cl. ..................................... 250/201.3; 356/72
(58) Field of Search ........................ 250/201.2–204.4, 250/237 G, 222.1, 573–575; 356/4.04, 4.05, 27, 28, 28.5, 72, 73; 396/79–82; 348/352, 354–356

(56) References Cited

U.S. PATENT DOCUMENTS 2,772,479 A    12/1956   Doyle
3,432,237 A    3/1969    Flower et al. ................. 356/28
3,525,695 A    8/1970    Gamertsfelder et al.
3,706,494 A    12/1972   Gardner
3,711,200 A    1/1973    Maughmer .................... 356/28
3,832,059 A    8/1974    Iten .............................. 356/28
3,856,403 A    12/1974   Maughmer et al. ........... 356/28
3,922,069 A    11/1975   Kishikawa et al. ......... 359/633
3,953,126 A    4/1976    Kim et al. .................... 356/28
4,110,042 A  * 8/1978    Leitz ......................... 356/4.04

(Continued)

FOREIGN PATENT DOCUMENTS

WO    WO 00/42412    7/2000    .......... G01N/15/02

OTHER PUBLICATIONS

Kubota, Fumio et al. 1995. "Flow Cytometer and Imaging Device Used in Combination." *Cytometry*: 21:129–132.

(Continued)

*Primary Examiner*—Stephone B. Allen
*Assistant Examiner*—Stephen Yam
(74) *Attorney, Agent, or Firm*—Ronald M. Anderson

(57) ABSTRACT

A pair of optical gratings are used to modulate light from an object, and the modulated light from either optical is used to determine the velocity of the object. Each optical grating is offset from a reference focal point by the same distance, one grating being offset in a positive direction, the other in a negative direction. Signals produced in response to the modulated light can be processed to determine a direction in which a primary collection lens should be moved in order to improve a focus of the imaging system on the object. The lens is moved incrementally in the direction so determined, and the process is repeated until an optimal focus is achieved. In a preferred embodiment, the signals are weighted, so that the optical grating disposed closest to the optimal focus position contributes the most to velocity detection.

29 Claims, 35 Drawing Sheets

U.S. PATENT DOCUMENTS

| | | | |
|---|---|---|---|
| 4,148,585 A | 4/1979 | Bargeron et al. | 356/28.5 |
| 4,729,109 A | 3/1988 | Adrian et al. | 364/560 |
| 4,770,992 A | 9/1988 | Van den Engh et al. | 435/6 |
| 4,786,165 A | 11/1988 | Yamamoto et al. | 356/23 |
| 5,014,131 A | 5/1991 | Reed et al. | |
| 5,054,913 A | 10/1991 | Ishikawa et al. | 356/28.5 |
| 5,096,807 A | 3/1992 | Leaback | 435/6 |
| 5,141,609 A | 8/1992 | Sweedler et al. | 356/344 |
| 5,159,397 A | 10/1992 | Kosaka et al. | 356/73 |
| 5,159,398 A | 10/1992 | Maekawa et al. | 356/73 |
| 5,159,642 A | 10/1992 | Kosaka | 382/6 |
| 5,160,976 A | 11/1992 | Carr et al. | 356/349 |
| 5,229,830 A | 7/1993 | Ishida et al. | 356/28.5 |
| 5,247,339 A | 9/1993 | Ogino | 356/73 |
| 5,247,340 A | 9/1993 | Ogino | 356/73 |
| 5,272,354 A | 12/1993 | Kosaka | 250/574 |
| 5,333,044 A | 7/1994 | Shaffer | 356/28 |
| 5,422,712 A | 6/1995 | Ogino | 356/73 |
| 5,444,527 A | 8/1995 | Kosaka | 356/73 |
| 5,471,294 A | 11/1995 | Ogino | 356/73 |
| 5,491,642 A | 2/1996 | Wormell et al. | |
| 5,548,395 A | 8/1996 | Kosaka | 356/73 |
| 5,596,401 A | 1/1997 | Kusuzawa | 356/23 |
| 5,633,503 A | 5/1997 | Kosaka | 250/458.1 |
| 5,644,388 A | 7/1997 | Maekawa et al. | 356/73 |
| 5,674,743 A | 10/1997 | Ulmer | 435/287.2 |
| 5,695,934 A | 12/1997 | Brenner | 435/6 |
| 5,754,291 A | 5/1998 | Kain | 356/344 |
| 5,760,899 A | 6/1998 | Eismann | 356/326 |
| RE35,868 E | 8/1998 | Kosaka | 250/574 |
| 5,831,723 A | 11/1998 | Kubota et al. | 356/73 |
| 5,848,123 A | 12/1998 | Strommer | 378/98.8 |
| 5,855,753 A | 1/1999 | Trau et al. | 204/484 |
| 5,859,694 A | 1/1999 | Galtier et al. | 356/28.5 |
| 5,929,986 A | 7/1999 | Slater et al. | 356/326 |
| 5,959,953 A | 9/1999 | Alon | 369/44.41 |
| 5,982,478 A | 11/1999 | Ainsworth et al. | |
| 6,007,994 A | 12/1999 | Ward et al. | 435/6 |
| 6,014,468 A | 1/2000 | McCarthy et al. | 382/254 |
| 6,066,459 A | 5/2000 | Garini et al. | 435/6 |
| 6,116,739 A | 9/2000 | Ishihara et al. | 353/31 |
| 6,156,465 A | 12/2000 | Cao et al. | 430/30 |
| 6,210,973 B1 | 4/2001 | Pettit | 436/172 |
| 6,211,955 B1 | 4/2001 | Basiji et al. | 356/326 |
| 6,249,341 B1 | 6/2001 | Basiji et al. | 356/73 |
| 6,256,096 B1 | 7/2001 | Johnson | 356/335 |
| 6,330,081 B1 | 12/2001 | Scholten | 358/463 |
| 6,381,363 B1 | 4/2002 | Murching et al. | 382/164 |
| 6,522,781 B1 | 2/2003 | Norikane et al. | 382/203 |
| 2001/0006416 A1 | 7/2001 | Johnson | 356/73 |
| 2002/0126275 A1 | 9/2002 | Johnson | 356/317 |

OTHER PUBLICATIONS

Kubota, F. 2003. "Analysis of red cell and platelet morphology using an imaging–combined flow cytometer." *Clin. Lab. Haem.*: 25:71–76.

Ong, Sim Heng. 1985. Development of a System for Imaging and Classifying Biological Cells in a Flow Cytometer. Doctor of Philosophy Thesis. University of Sydney. School of Electrical Engineering. (Aug.).

Ong, S.H. et al. 1987. "Development of an Image Flow Cytometer." *Analytical and Quantitative Cytology and Histology.* XIVth International Conference on Medical and Biological Engineering and the VIIth International Conference on Medical Physics, Finland. (Aug.): 375–382.

Ong, S.H. and P.M. Nickolls. 1991. "Optical Design in a Flow System For Imaging Cells." *Sciences in Medicines*: 14:2:74–80.

Ong, S.H. and P.M. Nickolls. 1994. "Analysis of MTF Degradation in the Imaging of Cells in a Flow System." *International Journal of Imaging Systems & Technology*: 5:243–250.

Satoh, Kaneo et al. 2002. "Small Aggregates of Platelets Can Be Detected Sensitively by a Flow Cytometer Equipped With an Imaging Device: Mechanisms of Epinedrine–Induced Aggregation and Antiplatelet Effects of Beraprost." *Cytometry*: 48:194–201.

Wang, Fu–sheng and Fumio Kubota. 2002. "A Novel Apoptosis Research Method With Imaging–Combined Flow Cytometer and HITC OR IR–125 Staining." *Cytometry*: 50:267–274.

Wietzorrek, Joachim et al. 1999. "A New Multiparameter Flow Cytometer: Optical and Electrical Cell Analysis in Combination With Video Microscopy in Flow." *Cytometry*: 35:291–301.

\* cited by examiner

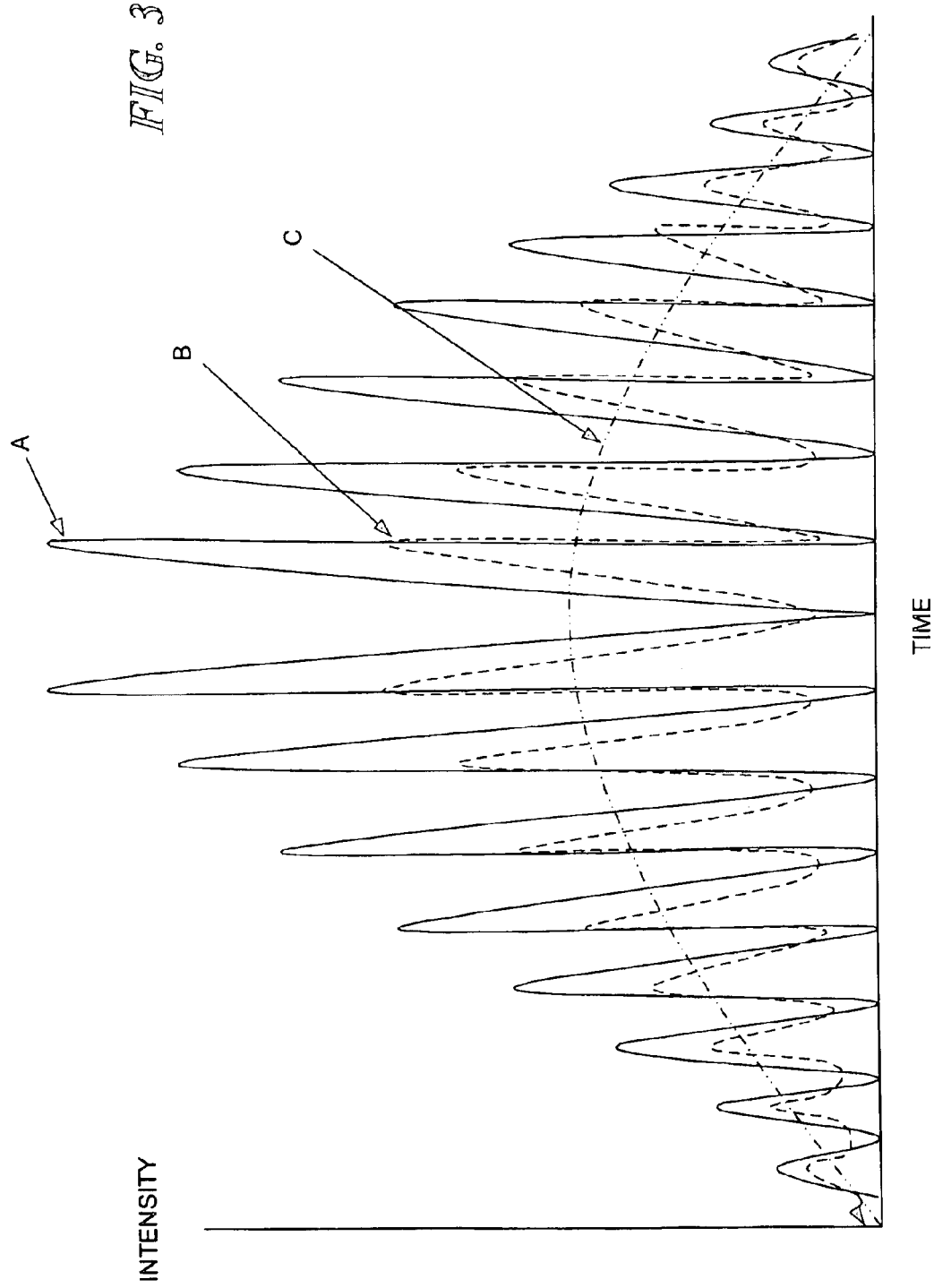

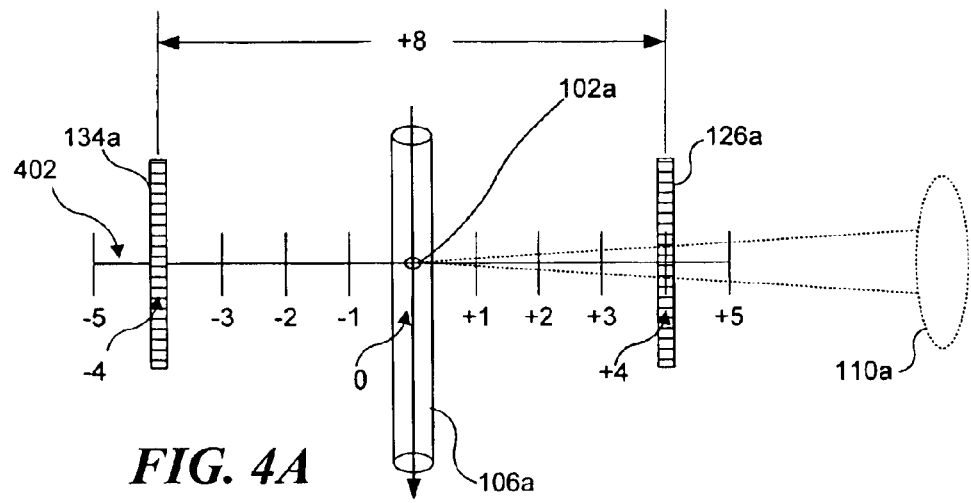
FIG. 4A
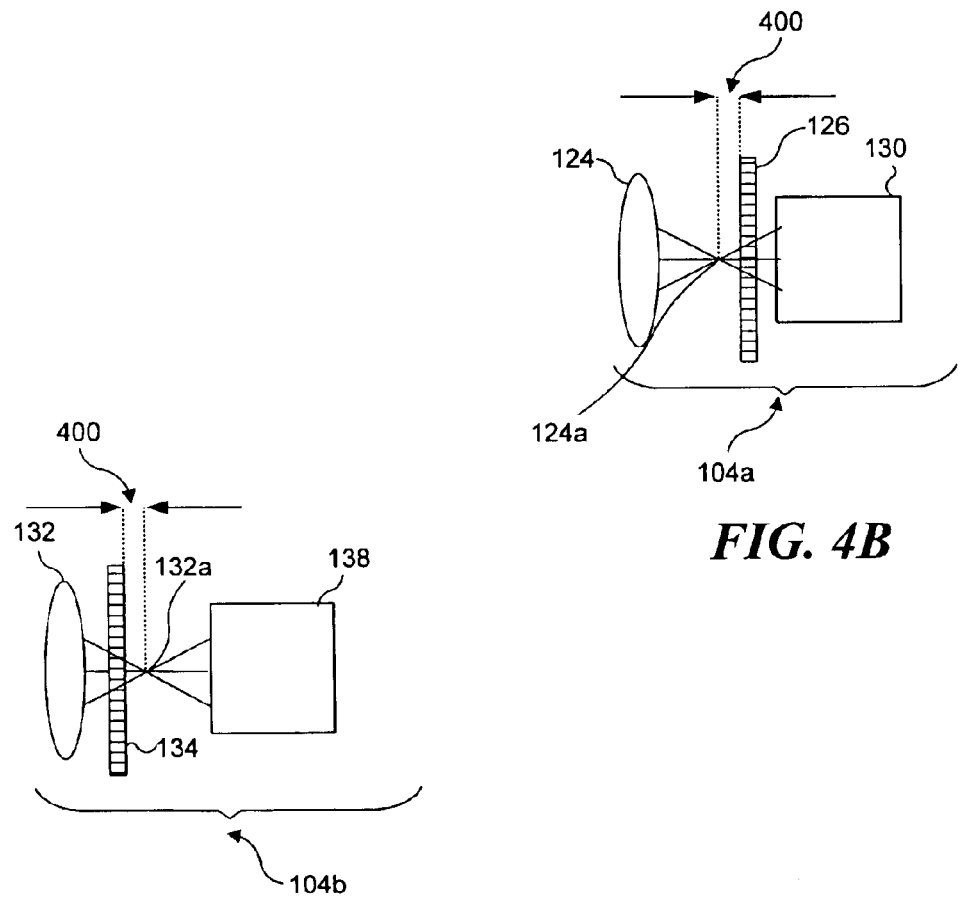
FIG. 4B
FIG. 4C

FOCUS PERFORMANCE
NOISE(0.05) OBJECT RATE(50)
SPACING(2) PITCH(5) BEADSIZE(1)

FOCUS PERFORMANCE
NOISE(0.05) OBJECT RATE(50)
SPACING(4) PITCH(5) BEADSIZE(1)

FOCUS PERFORMANCE
NOISE(0.05) OBJECT RATE(50)
SPACING(6) PITCH(5) BEADSIZE(1)

FOCUS PERFORMANCE
NOISE(0.05) OBJECT RATE(50)
SPACING(8) PITCH(5) BEADSIZE(1)

FOCUS PERFORMANCE
NOISE(0.05) OBJECTRATE(50)
SPACING(2) PITCH(10) BEADSIZE(1)

FOCUS PERFORMANCE
NOISE(0.05) OBJECTRATE(50)
SPACING(4) PITCH(10) BEADSIZE(1)

FOCUS PERFORMANCE
NOISE(0.05) OBJECTRATE(50)
SPACING(6) PITCH(10) BEADSIZE(1)

FOCUS PERFORMANCE
NOISE(0.05) OBJECTRATE(50)
SPACING(8) PITCH(10) BEADSIZE(1)

AUTO FOCUS FOR A FLOW IMAGING SYSTEM

RELATED APPLICATIONS

This application is based on a prior provisional application, Ser. No. 60/462,574, filed on Apr. 11, 2003 and is further a continuation-in-part of a prior conventional application Ser. No. 10/348,193, filed on Jan. 16, 2003, now U.S. Pat. No. 6,778,263, which itself is a continuation-in-part of a prior conventional application Ser. No. 09/939,292, filed on Aug. 24, 2001, now U.S. Pat. No. 6,532,061, which itself is based on a prior provisional application, Ser. No. 60/228,076, filed on Aug. 25, 2000, the benefit of the filing dates of all of which are hereby claimed under 35 U.S.C. § 119(e) and 35 U.S.C. § 120, as appropriate.

FIELD OF THE INVENTION

The present invention generally relates to a method and apparatus for automatically focusing an optical system, and more specifically, to a method and apparatus used to enable auto focusing of objects in flow, for a flow imaging system.

BACKGROUND OF THE INVENTION

Cells and groups of cells are three-dimensional objects containing rich spatial information. Many different analytical probes, which preferentially bind to specific target receptors within a cell, are available to identify the distribution of different bio-molecules within a cell. There is a growing interest in studying cells as dynamic structures including numerous interacting feedback control systems. Understanding cells as dynamic structures, as opposed to static structures, can lead to the development of new drugs, better diagnostic procedures, more effective therapies, and better health care management strategies. However, achieving this improved understanding will likely require the ability to extract a far greater amount of information from cells than can currently be achieved using existing tools.

The principal technologies for cellular analysis are automated microscopy and flow cytometry. The information generated by these mature technologies, while useful, is often not as detailed as would be desired. Automated microscopy enables two-dimensional (2D) imaging of from one to three colors of cells on slides. Typical video frame rates limit kinetic studies to time intervals of 30 ms. Instruments known as flow cytometers currently provide vital information for clinical medicine and biomedical research by performing optical measurements on cells in liquid suspension. Whole blood, fractionated components of blood, suspensions of cells from biopsy specimens and from cell cultures, and suspensions of proteins and nucleic acid chains are some of the candidates suitable for analysis by flow cytometry.

In flow cytometers that are specifically designed for routine blood sample analysis, cell type classification is performed by measuring the angular distribution of light scattered by the cells, and the absorption of light by specially treated and stained cells. The approximate numbers of red blood cells, white blood cells of several types, and platelets are reported as the differential blood count. Some blood-related disorders can be detected as shifts in optical characteristics, as compared to baseline optical characteristics, and these shifts are indicative of morphological and histochemical cell abnormalities. Flow cytometers have been adapted for use with fluorescent antibody probes, which attach themselves to specific protein targets, and for use with fluorescent nucleic acid probes, which bind to specific DNA and RNA base sequences by hybridization. Such probes find application in the medical field for the detection and categorization of leukemia, as well as application in the fields of biomedical research and drug discovery. By employing these prior art techniques, flow cytometry can measure four to ten colors from living cells. However, prior art flow cytometry offers little spatial resolution, and no ability to study a cell over time. There is clearly a motivation to address the limitations of cell analysis technologies by providing an imaging platform that is configured for high speed and high sensitivity cell imaging.

A key issue that arises in cell analysis carried out with imaging systems is the measurement of the velocity of a cell or other object through the imaging system. Thus, many such systems include velocity detection components. A particularly useful technology for measuring object velocity in fluids is based on the insertion of a grating with alternating opaque and transparent parallel bars in the light path of a photo-sensor. Light from moving objects is modulated by the optical grating pattern to create a signal with a frequency directly proportional to the component of velocity perpendicular to the optical grating bars. If object motion is constrained to this perpendicular direction, then the frequency is equal to the true velocity divided by the period, or pitch, of the optical grating. A laser velocimeter based on this principle for measuring the velocity of a reflective surface moving relative to the instrument is disclosed in U.S. Pat. No. 3,432,237, issued on Mar. 11, 1969, and entitled "VELOCITY MEASURING DEVICE." In the disclosed system of this patent, the target surface is illuminated with a continuous wave laser, and light scattered by the moving surface is collected by a lens and then delivered to a photosensitive detector through a grating. The bars of the optical grating are oriented perpendicular to the axis of motion. An electronic frequency measuring circuit is used to determine the frequency of the photosensitive detector. The frequency is conveyed directly to a display device for viewing and is converted to velocity.

An application of this method to objects suspended in fluid is disclosed in U.S. Pat. No. 3,953,126, issued on Apr. 27, 1976, and entitled "OPTICAL CONVOLUTION VELOCIMETER." In the disclosed apparatus of this patent, light collimated by a lens passes through the flow of fluid and is reflected by a mirror with alternating bars of reflective and absorptive material. The reflective bars return light through the flow of fluid for collection by the lens. The lens focuses the reflected light on a photosensitive detector. An electronic circuit is used to estimate the frequency of the detector signal and to deliver the frequency to a display device for viewing as a velocity.

It should be noted that the hardware signal processors used in early implementations of laser velocimeters have largely been displaced by computation-based digital signal processors. The demands on the photosensor signal processors vary with the nature of the application, but the most stringent applications demand high speed and high accuracy, under conditions of low SNR and rapidly varying flow velocity.

An example of an effective method for extracting velocity from the photosensor signal of a grating-based laser velocimeter is disclosed in U.S. Pat. No. 5,859,694, issued on Jan. 12, 1999, and entitled "OPTICAL VELOCIMETER PROBE." In this patent, the digitized photosensor signal is captured in fblocks of samples for processing. For each block, the signal processor executes the steps of generating a complex signal using the Hilbert transform, autocorrelating the complex signal, and extracting the phase for each time sample of the auto-correlogram. The autocorrelation is performed using the steps of applying a complex Fourier transformation, squaring the magnitude of the spectrum, and then applying an inverse Fourier transformation. Finally, an optimization routine finds a best-fit velocity value for the 5 phase samples. The method described in this patent has the advantage of building SNR and delivering accurate velocity estimates, given long signal segments. However, the method is computation intensive, limiting the rate at which the velocity estimate is updated using readily available processors.

Particularly useful implementations for modulating light from moving objects to measure their velocity, by inserting a periodic grating into the detector path, are described in commonly owned and assigned U.S. Pat. Nos. 6,532,061 and 6,507,391, both entitled "MEASURING THE VELOCITY OF SMALL MOVING OBJECTS SUCH AS CELLS." Flow imaging systems described in these two patents are configured to enable hydrodynamic focusing of a sample fluid within a flow cell. Light from objects entrained in a fluid passing through the flow cell is modulated by an optical grating to enable an indication of a velocity of the objects to be determined. That indication of velocity is employed to synchronize a time delay integration (TDI) detector to the flow of the fluid (and of the objects entrained therein).

It is significant that the ability of a flow imaging systems to accurately determine velocity, such as by using an optical grating as disclosed in the above-noted references, is only one of the abilities that should be provided by a preferred flow imaging system for analyzing cells. The ability of such a flow imaging system to automatically ensure that objects in flow remain properly focused is also highly desirable. To further enhance the utility of flow imaging systems, such as those implementing velocity detection based on modulating light with an optical grating, it would therefore be desirable to provide a method and apparatus for implementing an auto focus ability in such flow imaging systems. Optimized and predefined focal settings in flow imaging systems can be degraded by shock, movement of optical elements over the life of the system, temperature expansion coefficients of optical elements and related components, and temporal frequency changes occurring within a hydrodynamically focused fluidic core.

SUMMARY OF THE INVENTION

The present invention enables auto focusing to be implemented in a flow imaging system that uses optical gratings to modulate light from an object so that the modulated light has a frequency proportional to the velocity of the object. A plurality of optical gratings and detectors are configured to achieve a first modulated light path and a second modulated light path. Each modulated light path is configured to receive light from the object and includes a detector, an optical grating configured to modulate the light such that the modulated light has a frequency proportional to the velocity of the object, and a focal point along the light path, where the object is in focus. In the first modulated light path, the optical grating is disposed in front of the first modulated light path's focal point, while in the second modulated light path; the optical grating is disposed behind the second modulated light path's focal point. For each of the first and second modulated light paths, when the light from the object is not in focus as it goes through the corresponding optical grating, the modulated light received at the corresponding detector will, in general (depending on the object size, grating pitch and spacing), be less modulated. By determining the modulation strength of signals corresponding to each of the modulated light paths, a Focus Function having a local minimum indicating the condition wherein the focal point of each modulated light path is equally distant from its corresponding detector can be determined. The Focus Function can be used to control the position of a lens directing light from the object into the flow imaging system, to ensure that objects flowing through a flow cell associated with the flow imaging system remain in focus.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein:

FIG. 1A schematically illustrates an auto focus system detecting light scattered by objects in flow;

FIG. 1B schematically illustrates an auto focus system detecting light emitted by fluorescence by the objects;

FIG. 1C schematically illustrates an auto focus system detecting the absorption of light by the objects;

FIG. 2A schematically illustrates a system including two optical paths used to achieve auto focusing and velocity detection;

FIG. 2B schematically illustrates a flow imaging system that performs velocity detection, synchronization of a TDI detector, and auto focusing;

FIG. 3 is a graph of time versus intensity, showing data for an optical grating disposed coincident with a reference focal point, and offset from the reference focal point by both a first and a second distance;

FIG. 4A schematically illustrates optical gratings offset from a reference focal point in object space;

FIGS. 4B and 4C schematically illustrate gratings offset from a reference focal point in real space;

Figure 22:
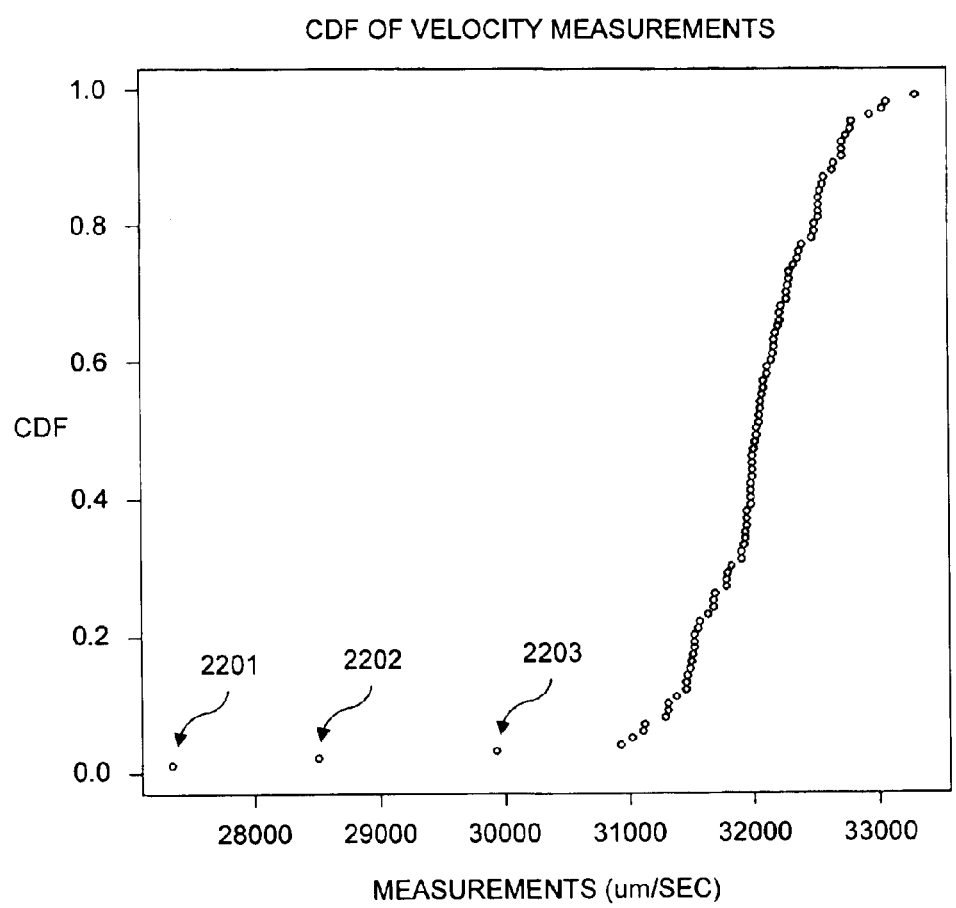
Figure 23A:
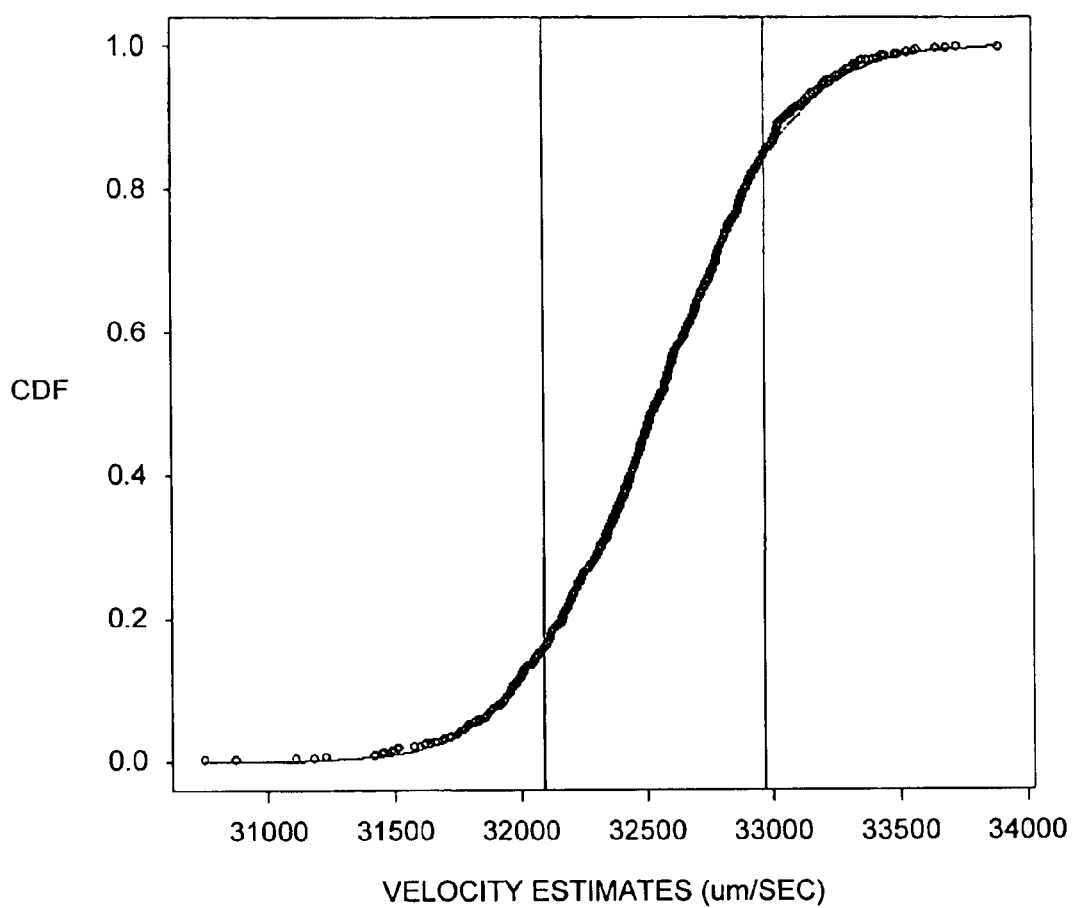
Figure 23B:
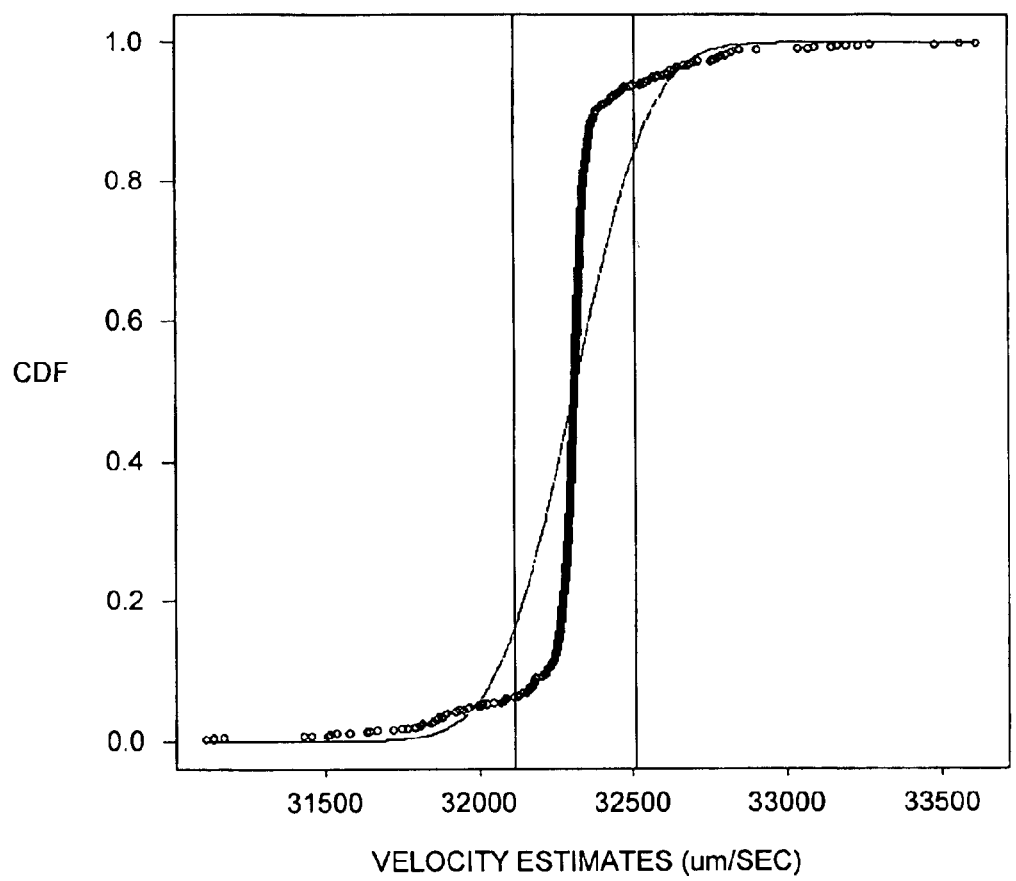
Figure 24:
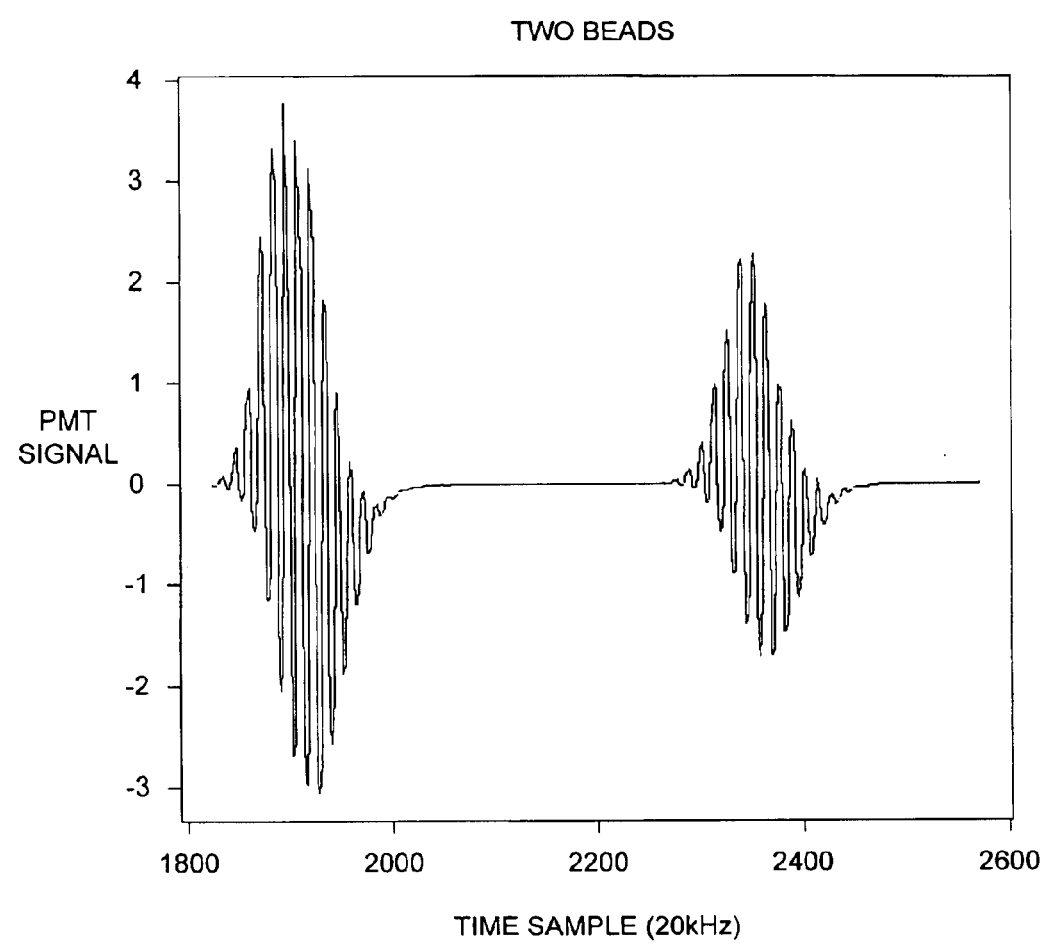
Figure 25:
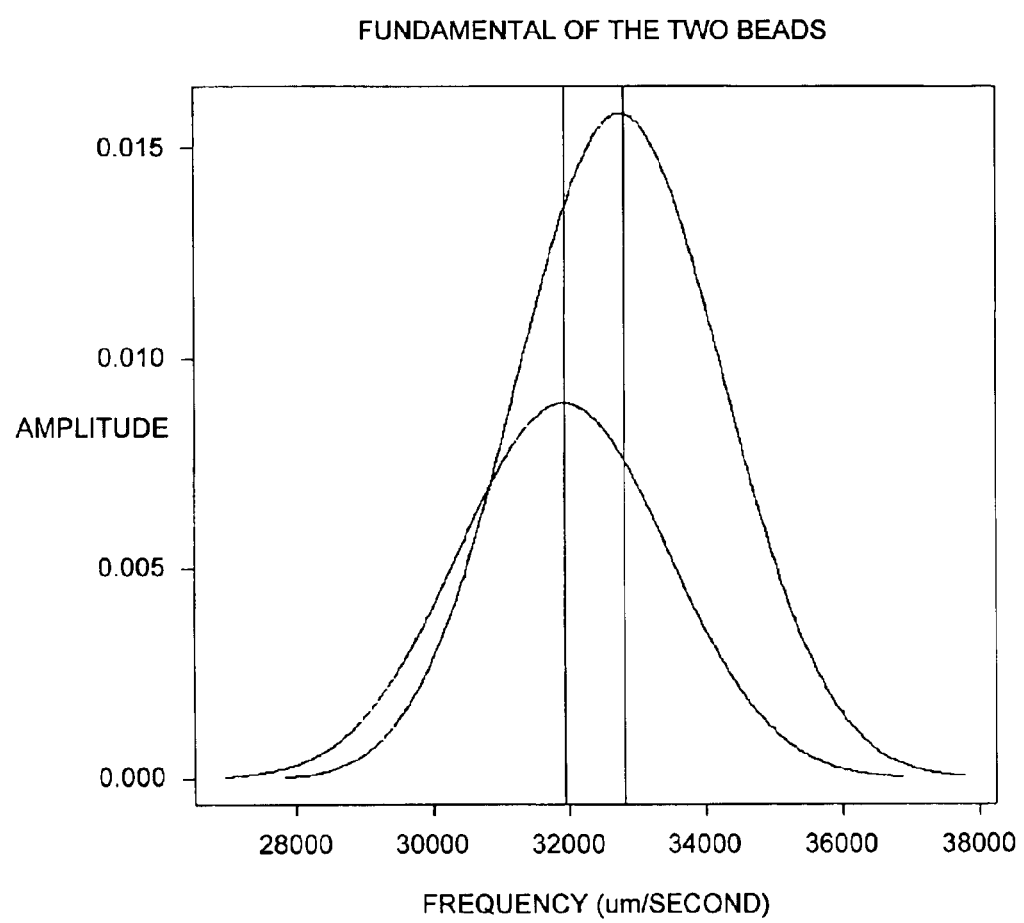
Figure 26:
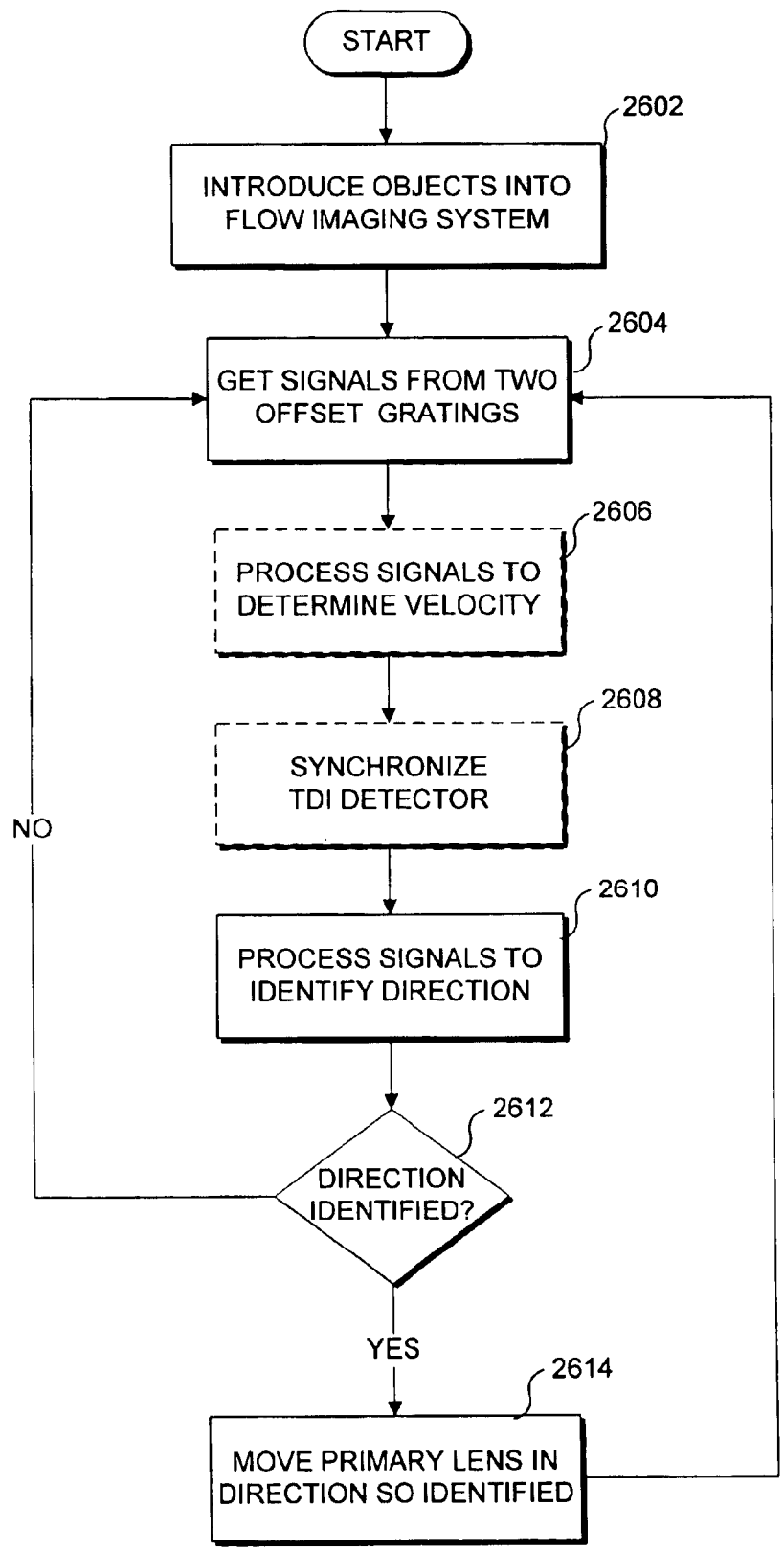

FIGS. 22, 23A, and 23B are graphs showing cumulative distribution functions based on sets of velocity measurements;

FIG. 24 is a graph showing empirical data from a flow imaging system including data corresponding to two beads;

FIG. 25 is a graph showing the determination of velocity for each bead of FIG. 24; and FIG. 26 is a flow chart showing the logical steps of the method for determining how to move a lens to auto focus the light from an object in accord with the present invention.

DESCRIPTION OF THE PREFERRED EMBODIMENT

Overview of the Present Invention

The present invention relates auto focusing systems and methods. Preferably, the present invention is implemented in a flow imaging system. However, the present invention can be used for applications not only where objects are entrained in a flow of fluid passing through an imaging system, but also wherever there is relative movement between objects of interest and the imaging system. In accord with the present invention, auto focusing is achieved by diverting light from an object along two optical legs (or more preferably, two light paths), each of which includes an optical grating that modulates light from the object such that the modulated light has a frequency proportional to the velocity of the object.

Each of the two modulation paths also includes a detector configured to receive the modulated light. The optical gratings are disposed in different positions in each modulation path relative to a point along each modulation path where an image of the object is in focus, such that light from the object that passes through each optical grating is not completely focused. The extent to which each optical grating modulates light from the object is a function of how well the light from the object is in focus as it passes through the grating. The more sharply in focus the light from the object is, the more modulated that light will be. The degree of modulation of light passing through each optical grating is determined by the detectors in each modulation path. Data from the detectors in each modulation path can be employed, as described in greater detail below, to manipulate optical components of the flow imaging system to ensure that the flow imaging system is properly focused on objects where there is relative motion between the imaging system and the objects.

A particularly preferred implementation of the present invention has been incorporated into flow imaging systems that are described in commonly owned and assigned U.S. Pat. Nos. 6,532,061 and 6,507,391, both entitled "MEASURING THE VELOCITY OF SMALL MOVING OBJECTS SUCH AS CELLS." The flow imaging systems described therein employ an optical grating to modulate light from an object (where there is relative motion between the object and the imaging system), and use the modulated light to determine the velocity of the relative motion. Particularly preferred implementations described therein use a signal indicative of the velocity so determined to synchronize a TDI detector to the relative motion. However, although a preferred implementation of the present invention is used in flow imaging systems that use an optical grating to determine velocity and synchronize a TDI detector, neither the determination of velocity nor the synchronization of a TDI detector are required to achieve auto focusing in accord with the present invention.

Figure 1A:
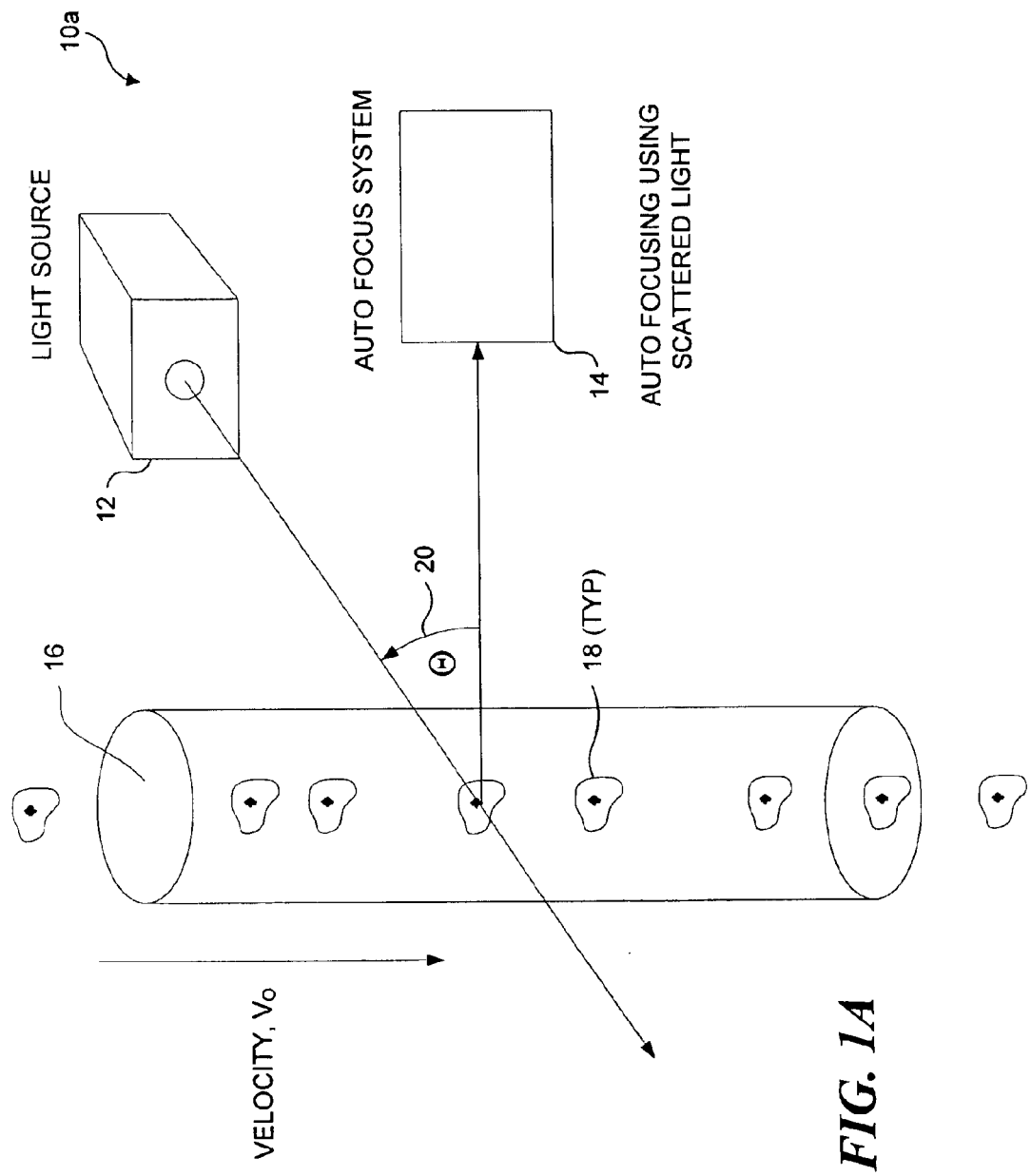
Figure 1B:
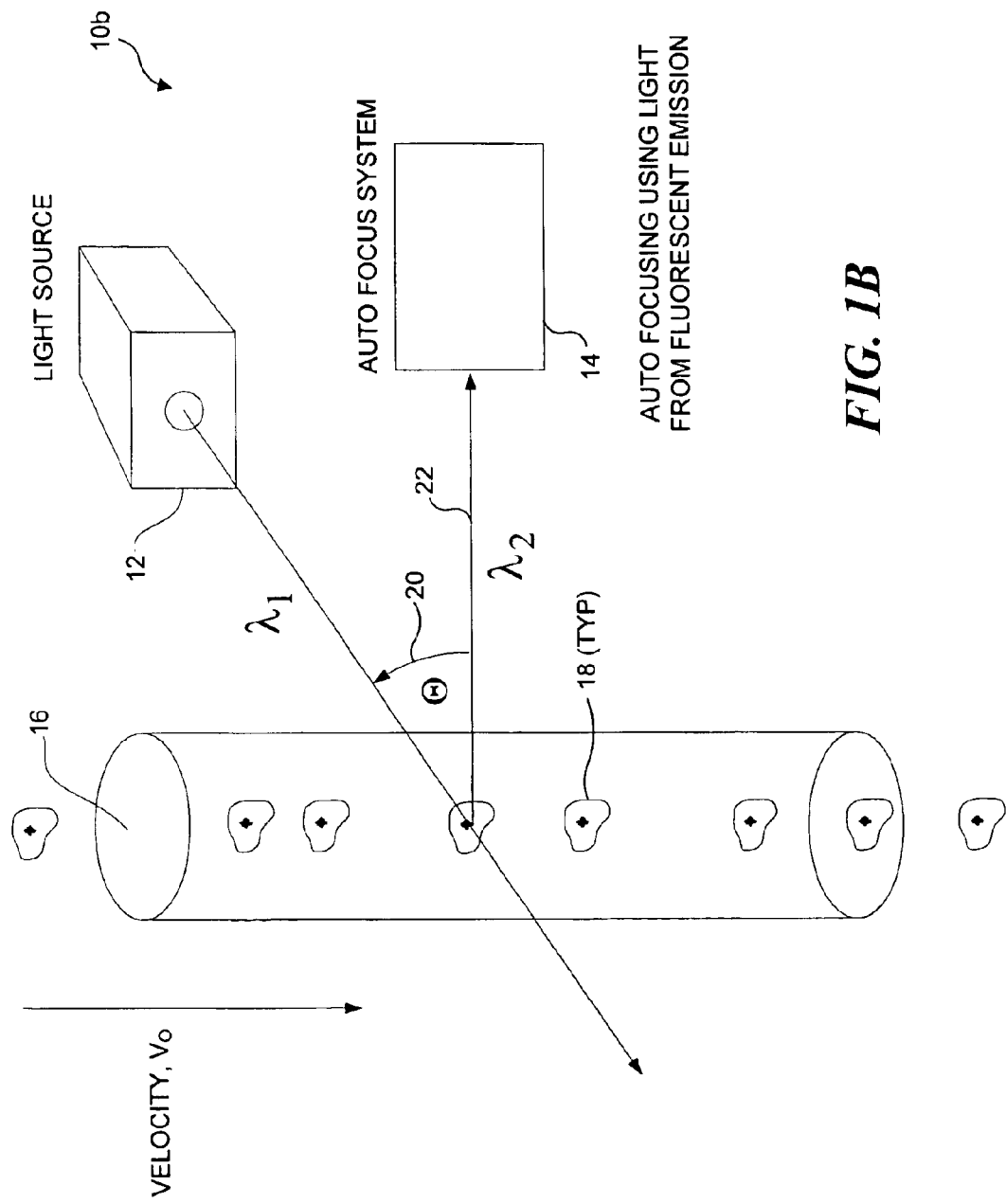
Figure 1C:
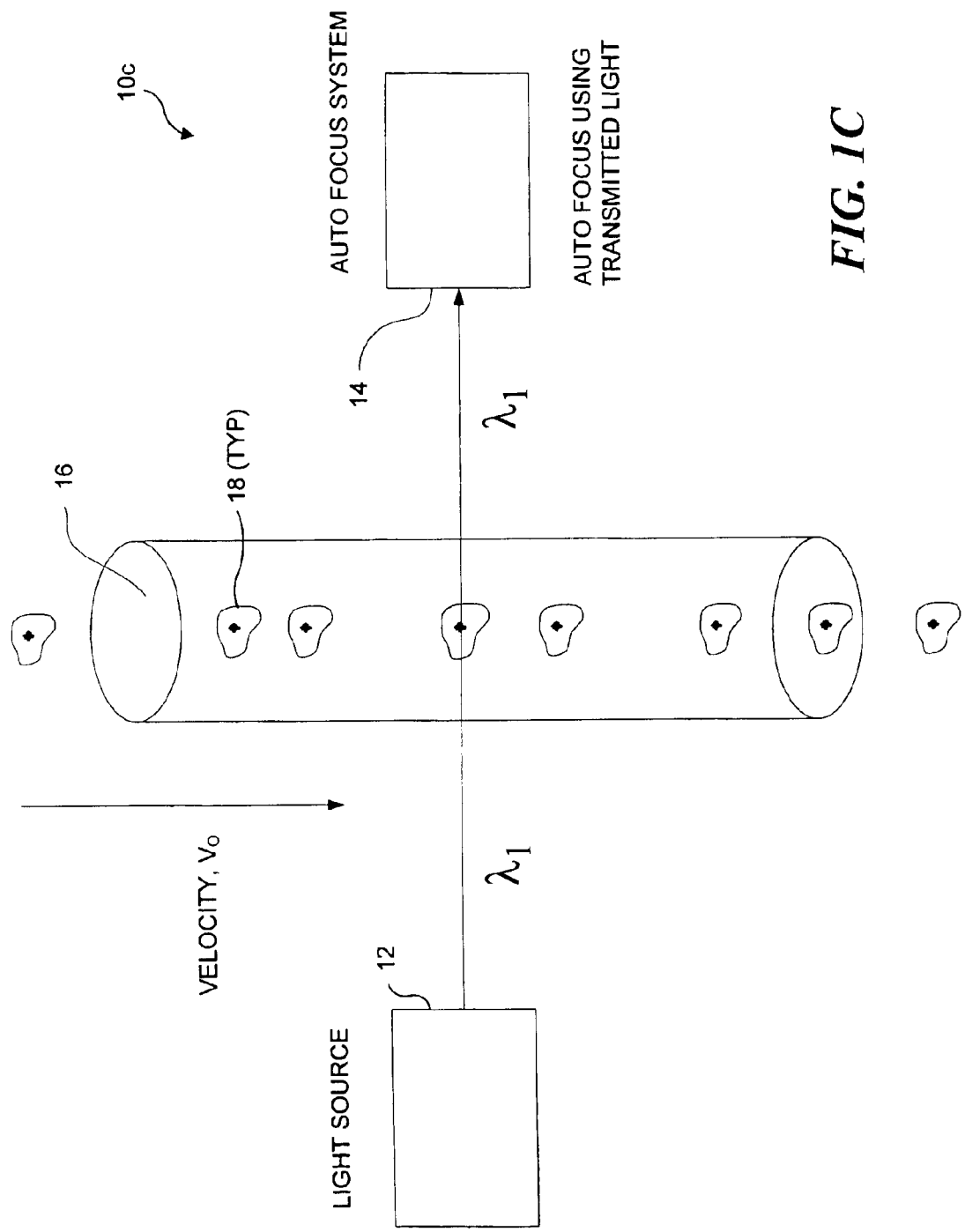

The present invention can be used with any of the various illumination and light collection configurations illustrated in FIGS. 1A–1C. However, those configurations should not be considered limiting on the scope of this invention and are provided merely as exemplary configurations. Each Figure shows a light source, objects in motion (preferably objects entrained in a flow of fluid) illuminated by the light source, and an auto focus system for receiving light from the objects. The light source may be a laser, a light emitting diode, a filament lamp, or a gas discharge arc lamp, and the system may include optical conditioning elements such as lenses, apertures, and filters that are employed to deliver one or more desired wavelengths of light to the object with an intensity required for auto focusing (and optionally, determining one or more other characteristics of the object). The auto focus system includes a light sensitive detector (not separately shown in these figures) comprising, for example, a photomultiplier tube or a solid-state photodetector, and one or more other optical conditioning elements such as a lens, an aperture, and/or a filter, to deliver the modulated light to the light sensitive detector (also not separately shown in these figures).

FIG. 1A illustrates the configuration of a system 10a that employs light scattered by objects 18 traveling through a flow tube 16. An angle 20 (designated as angle θ) between the beam axis of an illuminator 12 and an acceptance axis of a velocity detector 14 may be adjusted so that light scattered from the objects is delivered to the velocity detector, for a particular scatter angle. The intensity profile of the scattered light is a function of the ratio of the size of the scattering elements to the wavelength of the incident light. A relatively large number of scattering elements may be present in/on the object, and angle θ may be adjusted for the detection of scattered light from elements within a desired size range for the elements.

FIG. 1B illustrates the configuration of a system 10b that uses light emitted by objects 18 traveling in flow tube 16, in response to the absorption by the objects of light from illuminator 12. In this case, the detection axis will typically be orthogonal to the illumination axis in order to minimize the amount of incident light reaching velocity detector 14. Typically, a filter or a set of filters (not separately shown) will be included in the velocity detector to deliver to the light sensitive detector only a narrow band of wavelengths of the light traveling along a detection path 22 corresponding, for example, to the wavelengths emitted by the fluorescent or phosphorescent molecules in the object, so that light in the wavelength(s) provided by the illuminator 12 is substantially eliminated.

FIG. 1C illustrates the configuration of a system 10c utilizing light from illuminator 12 that continues to propagate towards velocity detector 14 along the axis of illumination; this light is modified by objects 18 traveling in flow tube 16 by absorption, diffraction, or refraction. System 10c is not well adapted for the detection of light emitted by fluorescence or phosphorescence, due to the high intensity of light emitted by illuminator 12 relative to the intensity of light emitted from objects 18, and because light from both sources follow the same path to velocity detector 14. Modification of the light by the objects caused by absorption can be detected by measuring the intensity of the light incident on the auto focus system. A system of lenses may be used to restrict the origin of the collected light to a desired field in the path of the stream of objects. Modification of the light by the objects caused by diffraction or refraction may be detected with a phase contrast method, in which only light subjected to phase modification by an object is visible, any unmodified light having been canceled by interference with a reference beam (not separately shown).

Figure 2A:
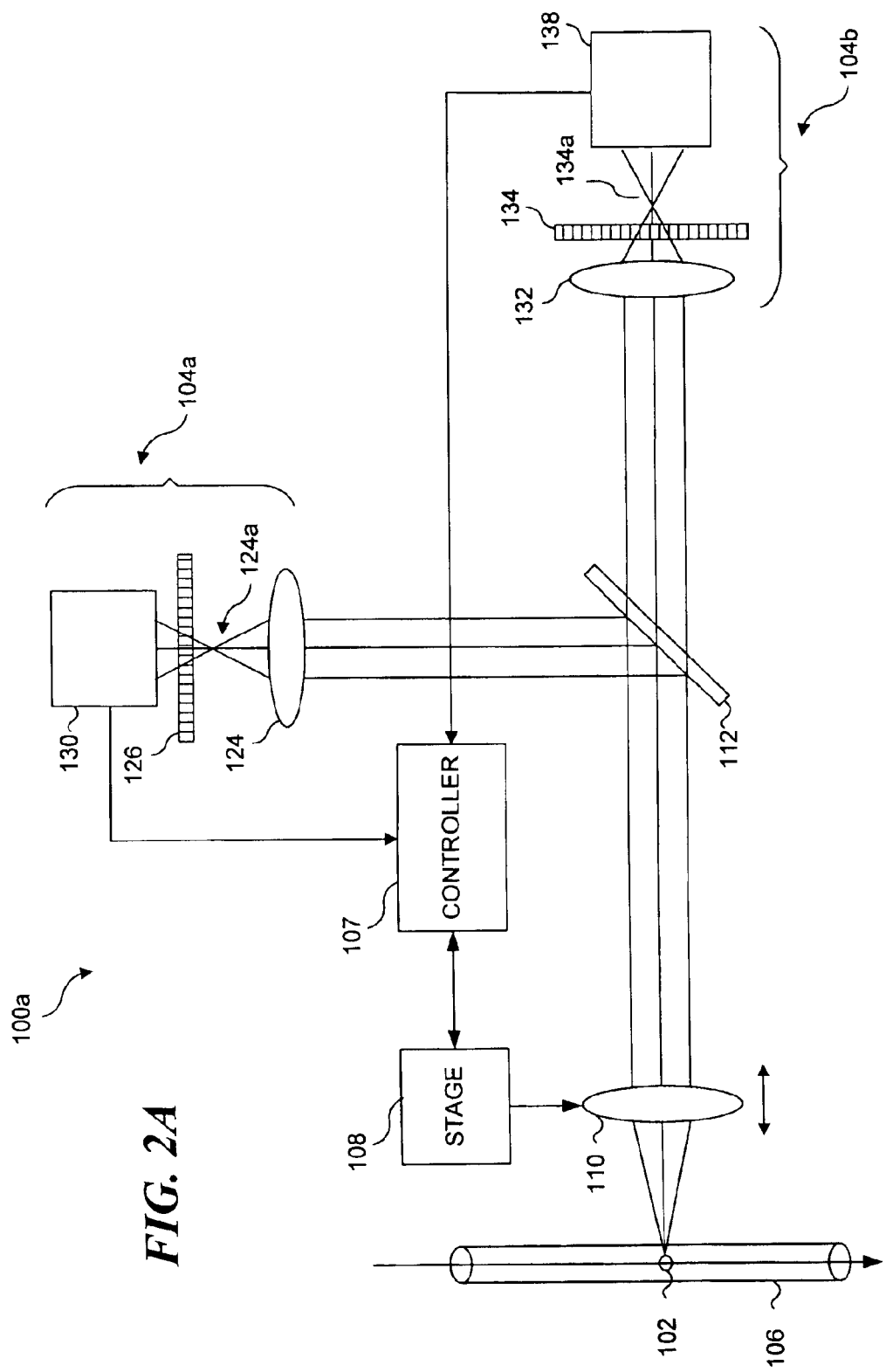

FIG. 2A schematically illustrates a flow imaging system 100a including an auto focusing subsystem. A primary lens 110 collimates scattered light from an object 102 passing through a flow cell 106. Lens 110 is coupled to a movable stage 108, so that a position of lens 110 can be adjusted. As discussed above in connection with FIGS. 1A–1C, various light sources can be used to illuminate object 102. A beam splitter 112 diverts a portion of the collimated light to achieve an optical path 104a, while light passing through beam splitter 112 continues on an optical path 104b, so that system 100a includes two optical paths used for auto focusing. Each optical path includes at least one lens element, an optical grating, and a detector. Path 104a includes a focusing lens 124. Focused light from lens 124 is transmitted through a grating 126. A detector 130, such as a photomultiplier tube (PMT), is located axially at the image of the system aperture stop. Path 104b similarly includes a focusing lens 132. Focused light from lens 132 is transmitted through a grating 134. A detector 138, such as a photomultiplier tube (PMT), is located axially at the image of the system aperture stop. Lens 124 has a corresponding focal point 124a, while lens 132 has a corresponding focal point 132a. Significantly, grating 126 is disposed farther away from lens 124 than focal point 124a. Grating 134 is disposed closer to lens 132 than focal point 132a. Optical path 104a and optical path 104b are configured such that absent gratings 126 and 134, detector 138 of path 104b and detector 130 of path 104a would provide equivalent signals. Because the gratings are inserted into different positions in each optical path, each detector generates a different signal. Each detector is logically coupled to a controller 107, which in turn is coupled to stage 108. Movement of lens 110 results in changes in the signals generated by detectors 130 and 138 (moving lens 110 changes the relative positions of focal points 124a and 132a). A function, which is described in greater detail below, relates the signals from the detectors to the proper focusing of object 102 by lens 110, and controller 107 can be used to control the position of stage 108 and lens 110 to ensure that objects passing through flow cell 106 remain properly focused. Controller 107 is preferably a computer or other programmed computing device; however, it should be understood that an application specific integrated circuit (ASIC) can alternatively be beneficially employed as a controller.

Figure 2B:
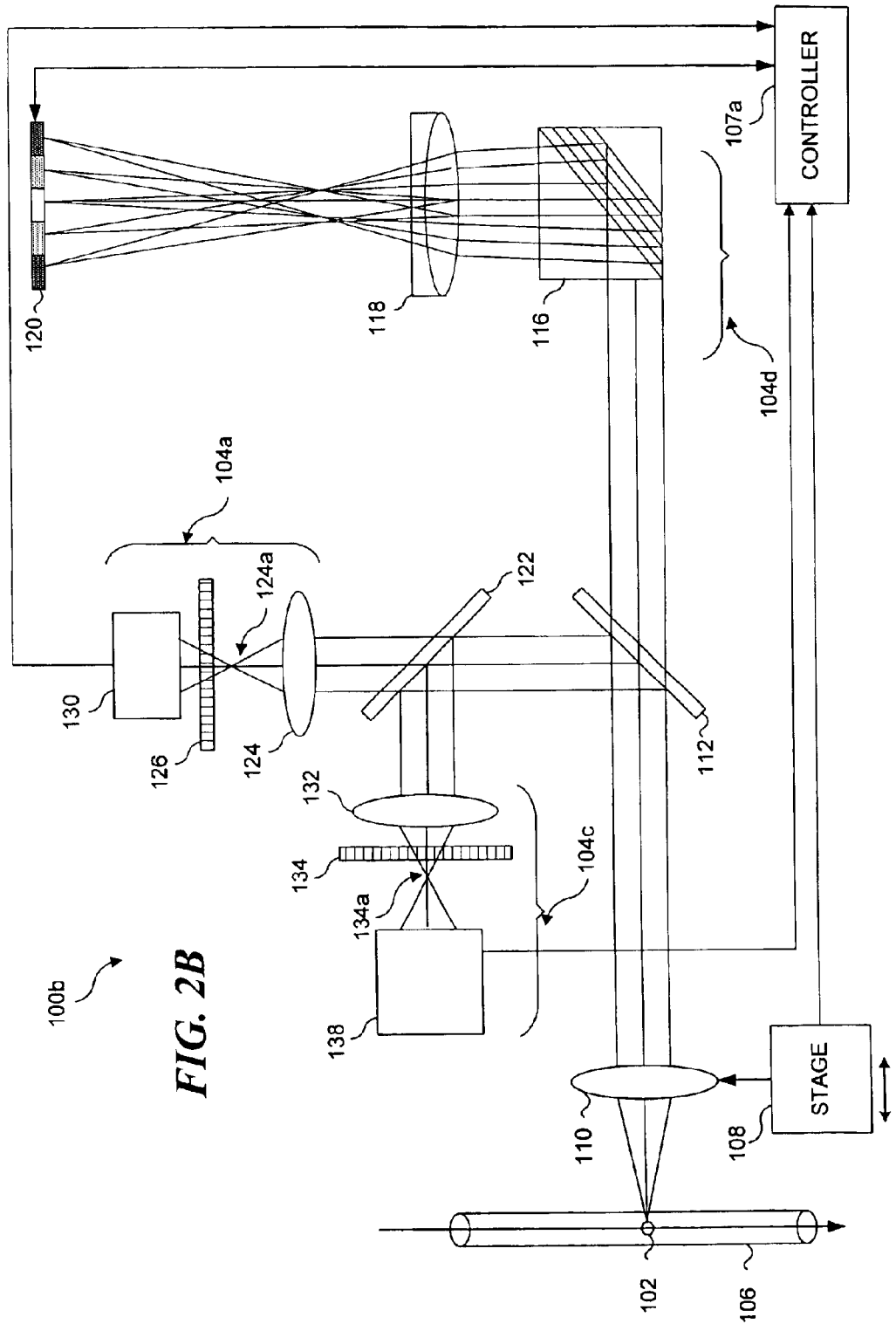

FIG. 2B schematically illustrates a flow imaging system 100b that performs velocity detection, synchronization of a TDI detector, and auto focusing. System 100b differs from system 100a in that one of the two optical paths of the auto focusing system has been moved, to enable an optical path 104d to be included. Optical path 104d includes a spectral decomposition filter 116, a lens 118, and a TDI detector 120. A beam splitter 122 has been added so some of the light directed toward optical path 104a (one optical path being used for auto focusing) is diverted to optical path 104c (another path being used for auto focusing). Controller 107a is configured to not only analyze signals from detectors 138 and 130 to ensure lens 110 is properly positioned, but also to employ the signals from detectors 130 and 138 to determine the velocity of object 102, and to synchronize TDI detector 120 to the motion of object 102.

Both FIGS. 2A and 2B show two optical paths with optical gratings being used to adjust a position of primary lens 110 along an x-axis. If desired, an additional pair of optical paths (not shown) with optical gratings can be employed to adjust a position of primary lens 110 along a y-axis (an axis parallel to the direction of the movement of object 102. Alternatively, a single pair of optical paths including an optical grating can be employed to adjust a position of primary lens 110 along only the y-axis, as opposed to only the x-axis. Empirical experience with flow imaging systems indicate that control of focus along the x-axis is more critical.

FIG. 3 schematically illustrates exemplary light intensity versus time curves for signals obtained from a detector in an optical path (such as optical paths 104a, 104b, and 104c of FIGS. 2A and 2B), when a grating is disposed at the focal point in the optical path, and when a grating is offset from the focal point in the optical path by both a first and a second distance. The intensity curves of FIG. 3 are based on the following assumptions: a particle size of 1 micron, a grating having 250 line base pairs per inch (a pitch of approximately 100 microns), a primary lens having a 4.5 mm focal length (see lens 110 of FIGS. 2A and 2B) that collimates the light from a particle in flow (see object 102 of FIGS. 2A and 2B) and a focusing lens (lenses 124 and 132 of FIGS. 2A and 2B) used to transmit light through the grating having a focal length (50 mm). The 12× magnification (f2 50 mm/f1 4.5 mm) of such an optical system results in an imaged grating appearing as having a 8.3 micron pitch in the object space of the 1 micron bead. Plot A assumes that the grating is located at the focus of the image (i.e. the image of object 102 at focal point 132a or focal point 124a of FIGS. 2A and 2B). Plot B assumes that the grating is displaced five microns on either side of the focal point, and Plot C assumes that the grating is displaced ten microns on either side of the focal point. The resultant modulation when the grating is in focus (i.e., Plot A) is characterized by having a maximum signal modulation or contrast. When the focal point and the grating are separated by 5 microns (i.e., Plot B), the modulation is decreased by 50%, and the baseline offset is increased. When the separation is increased to ten microns (i.e., Plot C, where the separation distance is equal to the grating pitch), there is no longer any modulation and the baseline offset is further increased.

If a Fast Fourier Transform (FFT) is performed on signals from detectors 130 and 138 of FIGS. 2A and 2B, the amplitude of the FFT will be maximized when the beam focus is minimized at the grating. Positioning gratings on either side of the focal point (see paths 104a and 104b in FIG. 2A, and paths 104a and 104c in FIG. 2B), a position of an object being imaged can be tracked using a focus function (described in detail below). Once the focus function of a flow imaging system is known, the focus function can be used to control the position of a stage that moves the collection lens, enabling the flow imaging system to continuously adjust the focus of the system to ensure objects in flow remain properly focused.

For flow imaging systems where the same optical gratings are used to enable auto focusing and velocity detection, a balance of grating pitch, object size (such as beads or particles) and grating spacing dimensions must be met. Empirical data has been collected to enable the effects of grating pitch and spacing dimensions upon focus performance to be analyzed. The empirical data collected indicate that optical gratings having about a 10 um pitch (it should be understood that the 10 um pitch dimension refers to the pitch dimension in the object space of the object in the flow cell; and for an optical system having 12× magnification, the image space dimension of such a grating will be 120 um), and paired optical gratings having a net grating offset of about 8 um (in the object space of the object being imaged; i.e. object 102 of FIGS. 2A and 2B) provide adequate performance for flow imaging system 100b (FIG. 2B). The concept of net offset is schematically illustrated in FIGS. 4A–4C FIG. 4A is based on object space (relative to the particles in flow, not the gratings), a theoretical construct that will be recognized by those of ordinary skill in the art. Object space is useful for examining relationships between optical elements. With an understanding of the properties of an optical system, dimensions developed based in object space can be applied to real world optical systems. In FIG. 4A, a flow cell 106a is disposed at a zero position along an X-axis 402. A lens 110a is positioned to collect light from an object 102a. A grating 126a is positioned at a +4 um position on the X-axis, while a grating 134a is disposed at a −4 um position on the X-axis. The net offset or separation distance between the gratings in FIG. 4A is thus 8 um. It should be understood that in the discussion below and the claims that follow, the terms "net offset" and "separation distance" apply to object space, as opposed to a physical dimension in an actual imaging system.

Relationships and dimensions defined in object space can be applied to imaging systems in image space. The dimensions in object space must be manipulated based on the imaging combination power of the optical system. If the axial or latitudinal magnification of the combination of lens 110 and either lens 124 or 132 of system 100a in FIG. 2 is 12×, then the longitudinal dimensions along the propagation axes determined in object space must be increased by the square of the latitudinal magnification ($12^2$) 144 fold. Referring to FIG. 4B, which shows optical path 104a of system 100a, focal point 124a in optical path 104a corresponds to the zero position on the X-axis in the object space diagram of FIG. 4A. Grating 126 is disposed 144*4 um=576 um from focal point 124, to correspond to +4 um in object space. Similarly, FIG. 4C shows optical path 104b of system 100a, and focal point 132a in optical path 104b corresponds to the zero position on the X-axis in the object space diagram of FIG. 4A. Grating 134 is disposed 144*4 um=576 um from focal point 124 (in the opposite direction), to correspond to −4 um in object space. Thus, with a 12× optical system, a net offset or separation distance of 8 um in object space corresponds to a physical distance of about 1152 um between the optical gratings.

For offset optical gratings to be effective in the present invention, the gratings (in object space and image space) need to be equidistant from a reference focal point, and on opposite sides of the reference focal point. In object space, the reference focal point is along the center axis of the flow cell, and the optical gratings are disposed on opposite sides of the flow cell. In image space, each optical path has its own reference focal point. In one optical path, the grating must be on the same side of the reference focal point as the reference focusing lens. In the second optical path, the grating must be on the opposite side of the reference focal point as the reference focusing lens. As noted above, each optical path should be equivalent in terms of lens magnification, lens numeric aperture, lens positions, detector sensitivity, and the amount of light received from the object. The only difference in the optical paths will be the relative positions of the optical gratings.

The following section discusses requirements of a focusing system in accord with the present invention, and presents the empirical data used to determine the suitability of the above noted optical grating. The basic operation of auto focusing systems in accord with the present invention can be broken down into two stages: initialization of a flow imaging instrument, and monitoring variations in the focus of sample objects over time. In the first stage, the flow imaging instrument must be able to identify a position for a primary collection lens (see lens 110 of FIGS. 2A and 2B) that enables objects passing though the flow cell of the flow imaging system to be generally in focus. As the first stage is for initialization, fine control of focus is not required, but the first stage must provide an indication of the direction the primary collection lens needs to be moved in order to improve the focus of objects passing through the flow cell. In the second stage, the flow imaging instrument adjusts the position of the primary lens to obtain a fine degree of focus (preferably to less than a micron error in object space).

To enable initialization and fine focus to be achieved, the net grating offset should preferably be as small as possible. To facilitate initialization, the optical gratings utilized in the auto focusing system (i.e., the optical gratings in each of the two optical paths) ought to be able to provide a signal that is robust to noise. For example, assume each optical grating in the auto focusing system is disposed such that there is a net grating offset of 4 um in object space, and the gratings enable a signal to be achieved such that the noise power level is equal to that of the signal obtained when the net grating offset is 8 um in object space. Then, initialization of the instrument will be successful if the primary collection lens coupled to the movable stage is less than +/−10 um (½ of 4 um+8 um) in object space away from a position of optimal focus.

Using a flow imaging system based on system 100 of FIG. 2A, empirical signal data was collected using 1 um beads as sample objects, and optical gratings having a pitch (as defined in the object space of the bead as shown in FIG. 4A) of 5 um in a first data set and 10 um in a second data set. When the 5 um grating was employed, it was determined that the signal obtained detectors 130/138 could not be distinguished from noise when the optical gratings were disposed about 4 um from the reference focal point in object space. When the 10 um grating was employed, it was determined that the signal obtained detectors 130/138 could not be distinguished from noise when the optical gratings were disposed about 8 um from the reference focal point in object space. Thus, to initialize the instrument when the primary collection lens is +/−10 um away from an optimal focus position, the gratings must be separated more than 8 um and 6 um, respectively, from the reference point, to initialize the instrument.

Empirical data were also collected using the same system and parameters, with random noise and multiple objects entering the flow cell. Such data indicates that gratings having a pitch of 10 um can be employed to initialize the instrument and enable auto focusing, but gratings having a pitch of 5 um do not perform as well.

Figure 5A:
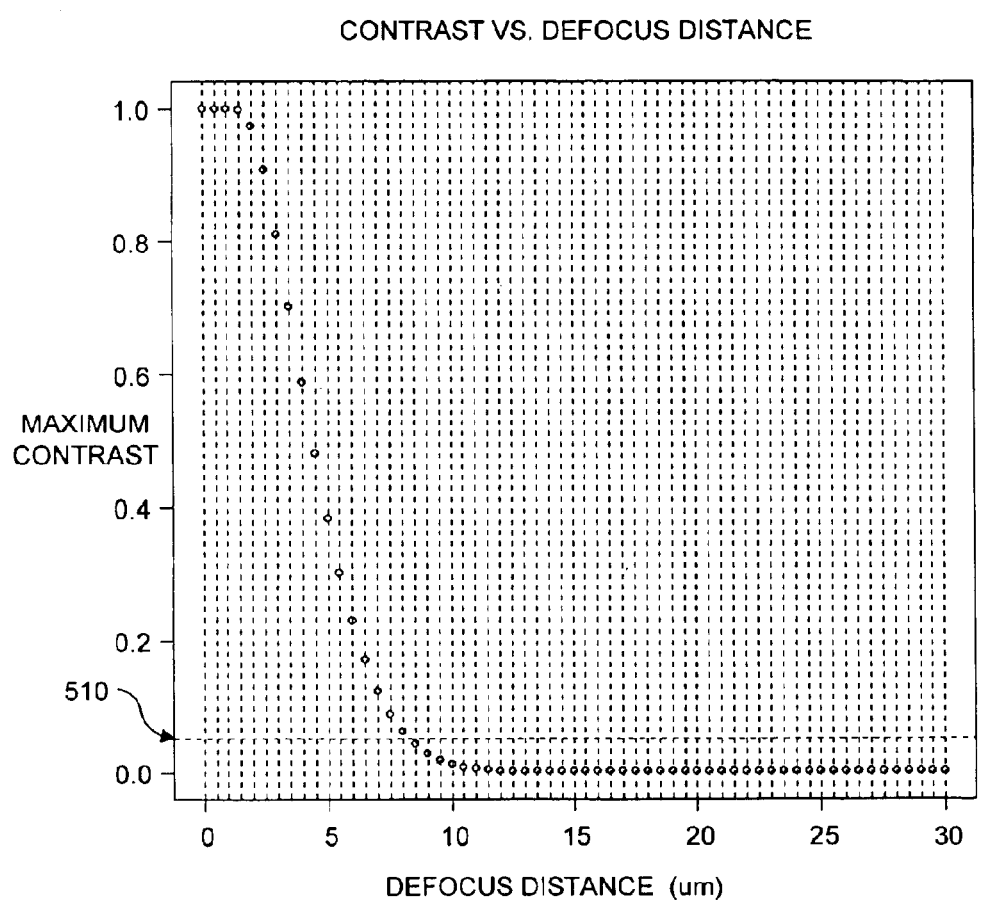
FIG. 5A is a graph of a contrast level of a 1 um diameter bead across a grating having a pitch of 10 um as a function of the bead's distance from the grating.

FIG. 5A graphically illustrates the contrast level of a 1 um diameter bead across a grating having a pitch of 10 um as a function of the bead's distance from the grating. The optical numerical aperture (NA) has a value of 0.7. A horizontal dash line 510 identifies the 0.05 contrast level that indicates the weakness of the signal when compared to a 0.05 noise level. In other words, data points below dash line 510 are not reliable when noise levels are equal or greater than about 5%. The contrast level is about 0.05 when the object is between about 8.0 um and about 8.5 um away from the grating (in object space) representing a total separation distance between the opposed gratings of 16–17 um (in object space).

Figure 5B:
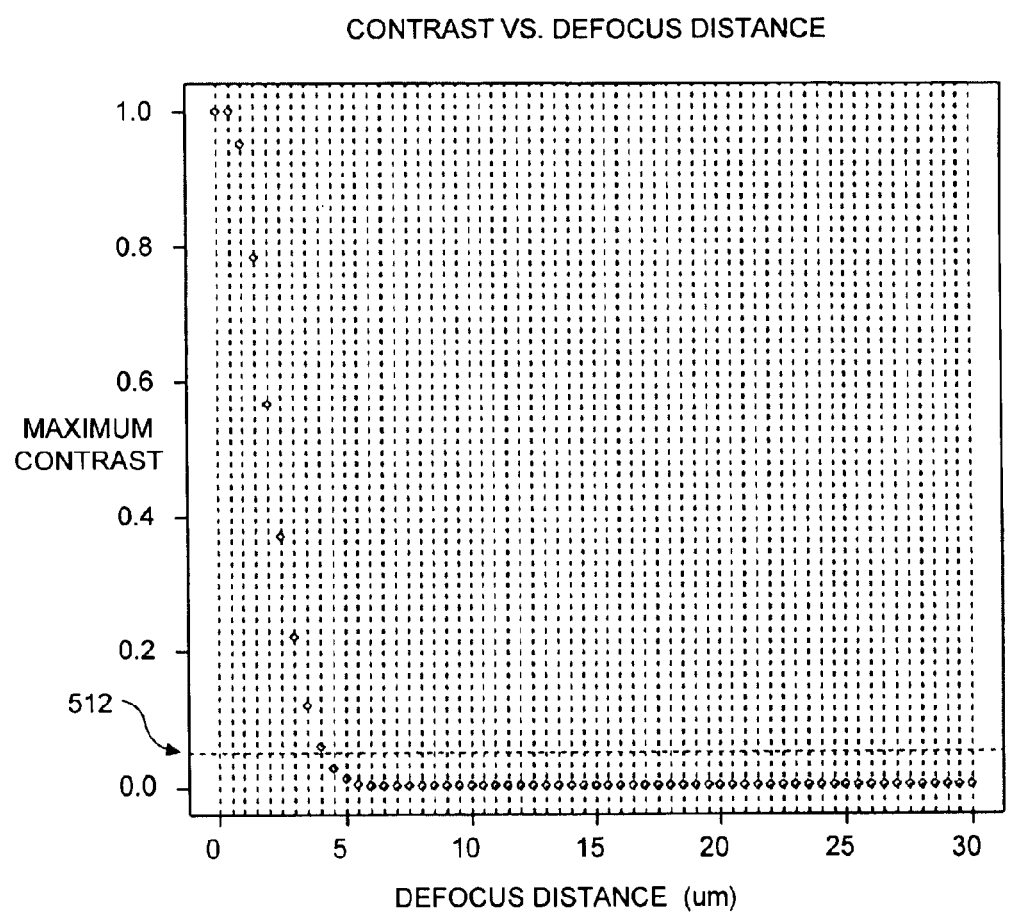
FIG. 5B is a graph of a contrast level of a 1 um diameter bead across a grating having a pitch of 5 um as a function of the bead's distance from the grating.

FIG. 5B similarly graphically illustrates the contrast level of a 1 um diameter bead across a grating having a pitch of 5 um as a function of the bead's distance from the grating. A horizontal dash line 512 denotes the 0.05 contrast level that indicates the weakness of the signal when compared to a 0.05 noise level. The contrast level is about 0.05 when the object is between about 4.0 um and about 4.5 um away from the grating (in object space) representing a total separation distance between the opposing gratings of 8–10 um (in object space).

As described in greater detail below, analysis of the 5 um and 10 um gratings indicates that the 5 um pitch grating will not be able to initialize the instrument if the focus is more than +/-10 um away from the optimum focus. It is shown below that the 10 um pitch grating has very good focus prediction performance around the optimum focus. Therefore, for the flow imaging system modeled, the 10 um pitch gratings are more effective.

Figure 6A:
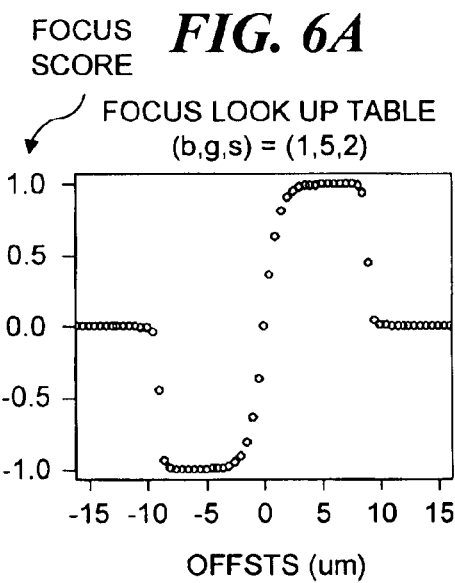
FIGS. 6A–6D are graphs of focus look up tables based on synthetic data for imaging 1 um diameter beads with an optical grating having a pitch of 5 um.
Figure 6B:
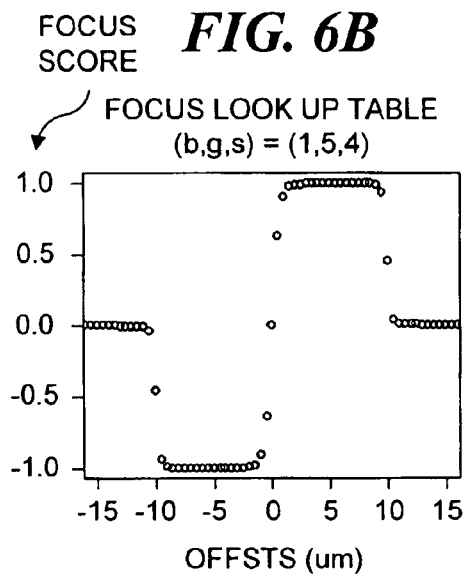
Figure 6C:
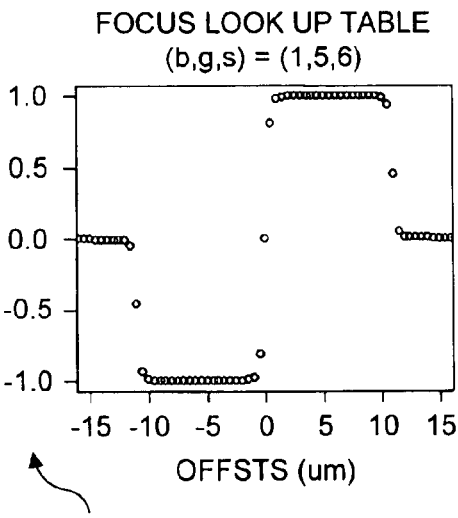
Figure 6D:
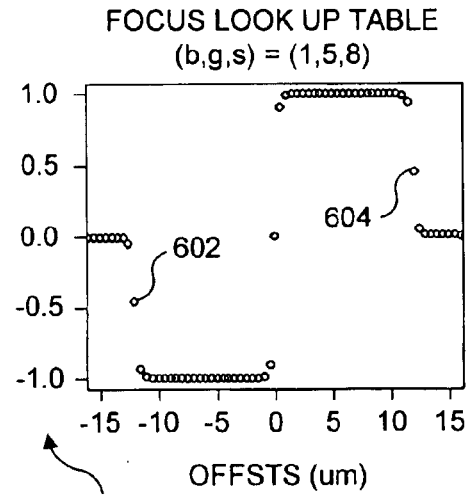

FIG. 6A–6D graphically illustrate focus look up tables based on synthetic data for imaging 1 um diameter beads with imaging system 100 a using optical gratings having a pitch of 5 um. FIG. 6A is based on a grating offset from a sample object by 2 um (in object space), FIG. 6B is based on a grating offset from a sample object by 4 um (in object space), FIG. 6C is based on a grating offset from a sample object by 6 um (in object space), and FIG. 6D is based on a grating offset from a sample object by 8 um (in object space). Note these values listed for the grating offset are representative of the total separation between the opposing gratings (in object space). Clearly the slope of the graph in FIG. 6D is steeper than the slope in the corresponding graphs of the other Figures, and thus, the 8 um separation from the grating and the object (in object space) is most desirable with its steep slope, and ability to detect out-of-focus directions from about +/-12 um, as indicated by points 602 and 604. However, the signals obtained using a 5 um grating are not very robust when the grating and object are separated by more than about 4.0 um to about 4.5 um (in object space), as indicated in FIG. 5B. Significantly, 8 um falls below line 512 in FIG. 5B, indicating that when noise levels are about 5%, that data collected when the distance between the grating and the object (in object space) is greater than about 4.0 um to about 4.5 um. Therefore, the focus table graphically illustrated in FIG. 6D will not be very reliable in the presence of noise (at levels of about 5%).

Figure 7A:
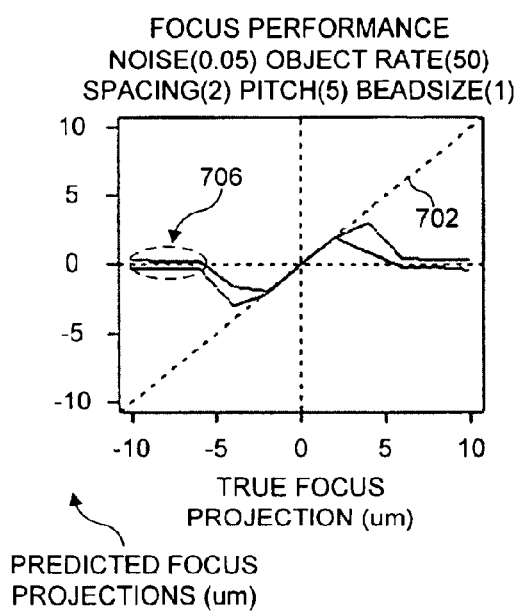
FIGS. 7A–7D are graphs of focus predictions based on introducing noise into the look up tables of FIGS. 6A–6D.
Figure 7B:
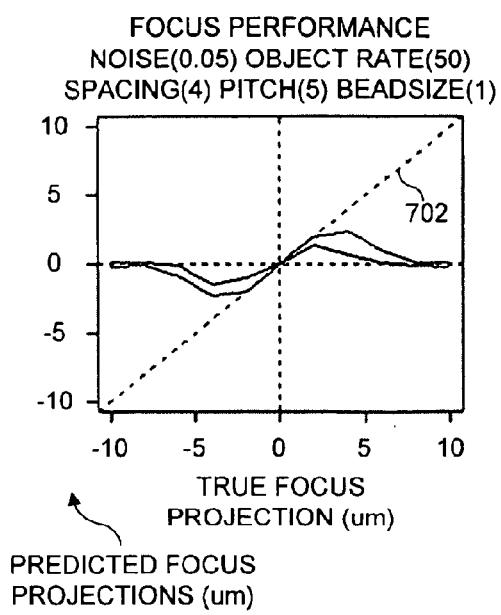
Figure 7C:
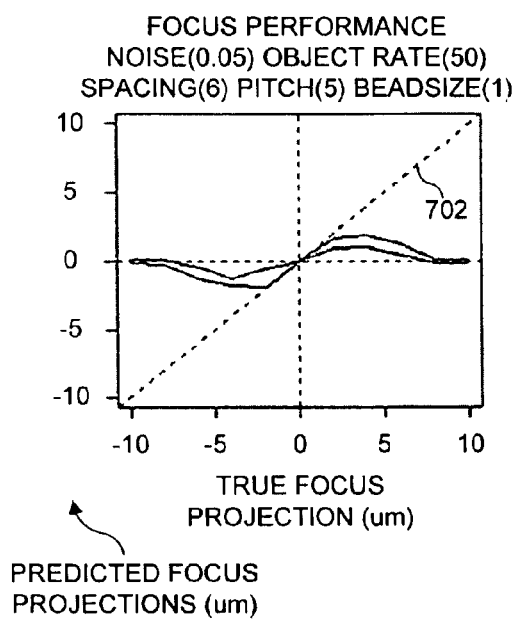

Each of the focus tables of FIGS. 6A–6D were subsequently analyzed by introducing Gaussian random noise at a level of 5%, and assuming a bead flow rate of 50 beads per second passing through a field of view of the imaging system. One hundred sample focuses were determined for each possible true focus projection. The extreme predicted focus projections (2% and 98% quantiles) are plotted in FIGS. 7A–7D and are shown as two lines in each Figure. Diagonal dash lines 702 in each of FIGS. 7A–7D are references corresponding to a perfectly focused system. FIG. 7A graphically illustrates projections based on a total grating offset from a sample object by 2 um (in object space), FIG. 7B graphically illustrates projections based on a total grating offset from a sample object by 4 um (in object space), FIG. 7C graphically illustrates projections based on a total grating offset from a sample object by 6 um (in object space), and FIG. 7D graphically illustrates projections based on a total grating offset from a sample object by 8 um (in object space).

With respect to FIGS. 7A–7D, each Figure includes an upper and lower curve. Where upper and lower curves in the same Figure converge, the focus predictions are accurate, and where the upper and lower curves diverge, predictions become poor. When the slope of the upper and lower curves approaches 0, then no directional information is available, and at that point, no determination can be made as to what direction the primary collection lens (such as lens 100a in FIG. 4A) needs to be moved to improve the focus.

FIG. 7A (2 um total grating offset) exhibits good focus predictions around the optimal focus indicated by line 702; however, beyond an offset of 5 um, the predictions become inaccurate. Thus, the 5 um grating at a noise level of 5% can only initialize the flow imaging instrument when the current focus position deviates from the optimal focus by less than 5 um. In a region 706, the slope of the upper and lower curves approaches zero, and thus, no directional information is available beyond +/-5 um.

Figure 7D:
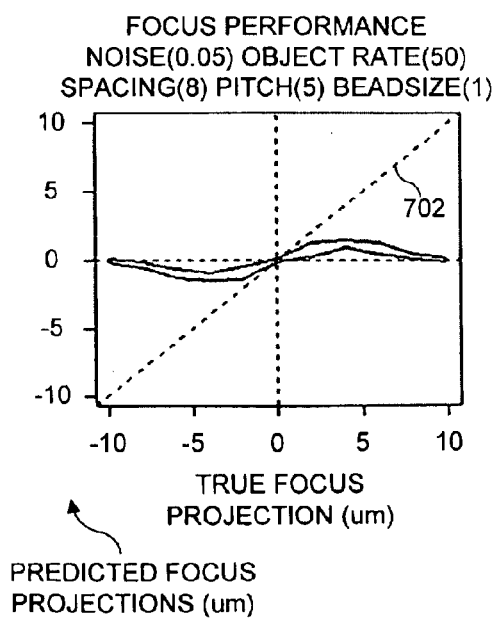

FIG. 7D (8 um total grating offset) exhibits poor focus predictions around the optimal focus indicated by line 702 (i.e., the upper and lower curves do not converge near line 702, as they do in FIG. 7A, near a region 708). In FIG. 7D, the slope of the upper and lower curves does not approach zero, and the instrument cannot be initialized when the current focus position deviates from the optimal focus by more than +/-5 um.

Figure 8A:
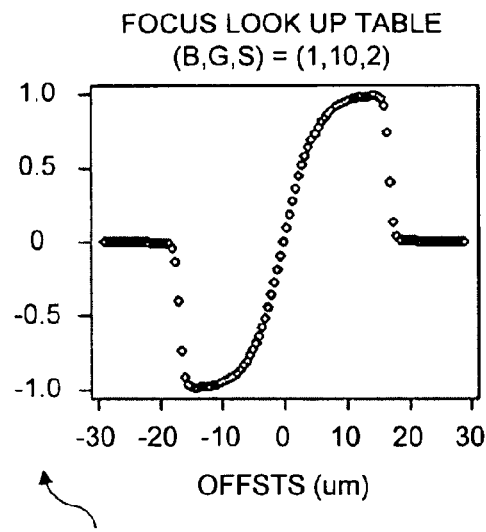
FIGS. 8A–8D are graphs of focus look up tables based on synthetic data for imaging 1 um diameter beads with an optical grating having a pitch of 10 um.
Figure 8B:
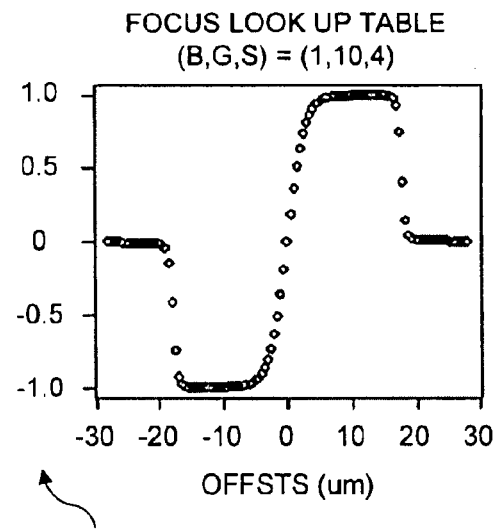
Figure 8C:
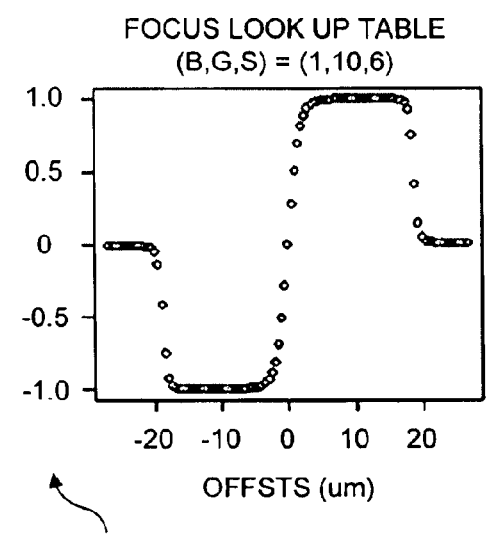
Figure 8D:
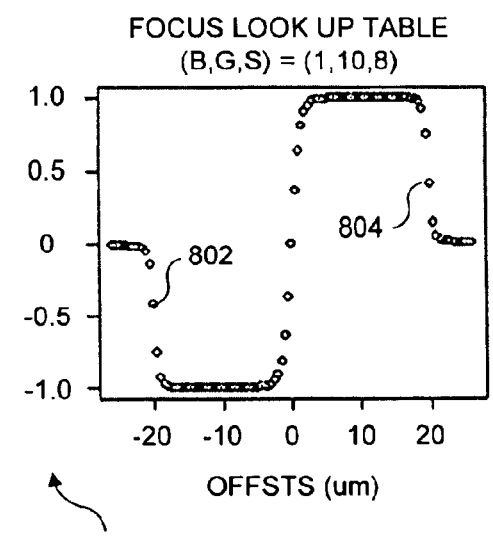

FIGS. 8A–8D graphically illustrate focus look up tables based on synthetic data for imaging 1 um diameter beads with imaging system 100a using optical gratings having a pitch of 10 um and are thus similar to FIGS. 6A–6D. FIGS. 9A–9D are similar to FIGS. 7A–7D, and again are based on optical gratings having a pitch of 10 um (in object space). FIG. 8A is based on a total grating offset of 2 um (in object space); FIG. 8B is based on a total grating offset of 4 um (in object space); FIG. 8C is based on a total grating offset of 6 um (in object space); and, FIG. 8D is based on a total grating offset of 8 um (in object space). Clearly, the slope in FIG. 8D is steeper than the slope in any other Figure, and thus, the 8 um grating offset is most desirable with its steep slope, and ability to detect out-of-focus directions based on +/-20 um, as indicated by points 802 and 804. The signals obtained using a 10 um grating are more robust than those obtained using a 5 um grating, such that as indicated in FIG. 5A. An 8 um offset does not fall under line 510 (line 510 corresponding to 5% noise, such that data points below line 510 are not reliable). As noted above, gratings having a pitch of 5 um produce unreliable data when noise is about 5% and the net grating offset is greater than about 4.0 um to about 4.5 um, as indicated in FIG. 5B. Thus the focus table of FIG. 8D is likely to be more reliable in the presence of noise (at levels of about 5%) than the focus table of FIG. 6D (5 um pitch grating).

Figure 9A:
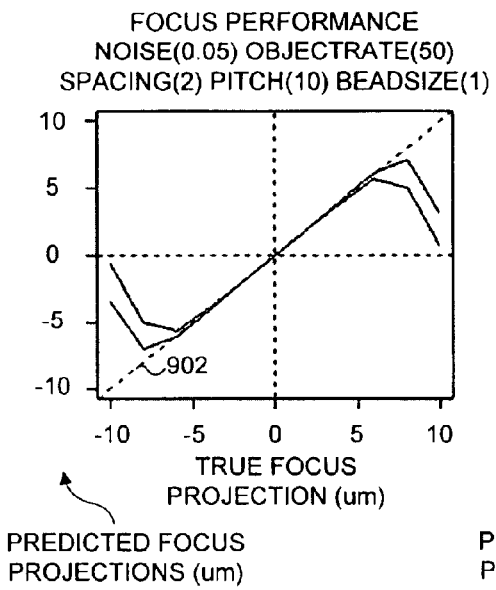
FIGS. 9A–9D are graphs of focus predictions based on introducing noise into the look up tables of FIGS. 8A–8D.
Figure 9B:
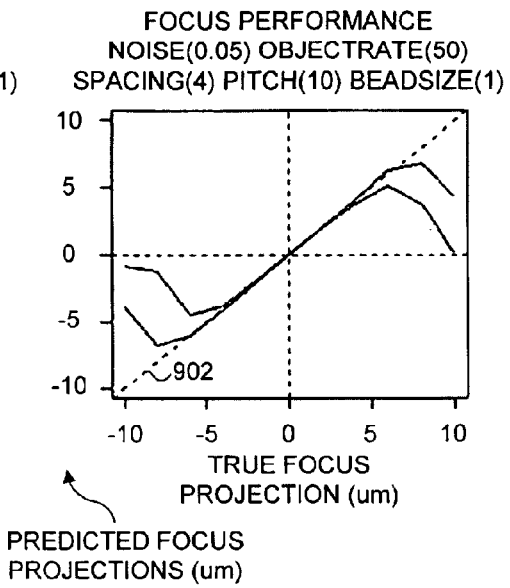
Figure 9C:
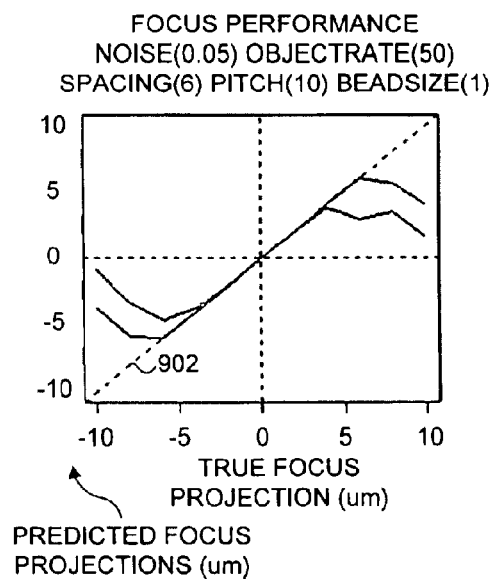

Each of the focus tables of FIGS. 8A–8D were subsequently analyzed by introducing Gaussian random noise at a level of 5%, and assuming a bead flow rate of 50 beads per second passing through a field of view of the imaging system. One hundred sample focuses were determined for each possible true focus projection. The extreme predicted focus projections (2% and 98% quantiles) are plotted in FIGS. 9A–9D and are shown as two lines in each Figure. Diagonal dash lines 902 in each of FIGS. 9A–9D are references corresponding to a perfectly focused system. FIG. 9A graphically illustrates projections based on a total grating offset of 2 um (in object space); FIG. 9B graphically illustrates projections based on a total grating offset of 4 um (in object space); FIG. 9C graphically illustrates projections based on a total grating offset of 6 um (in object space); and FIG. 9D graphically illustrates projections based on a total grating offset of 8 um (in object space).

Figure 9D:
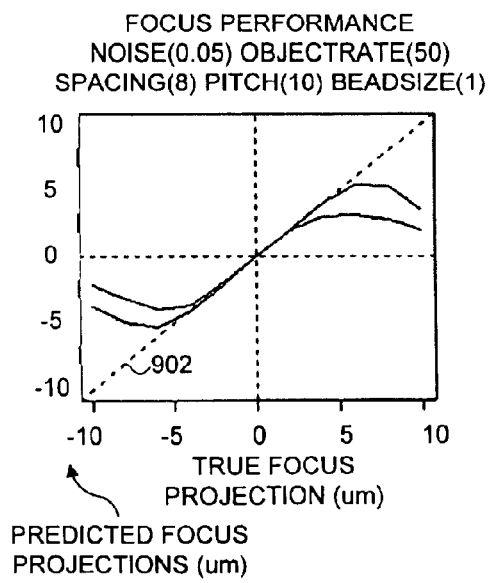

FIGS. 9A–9D each exhibit good focus predictions within a few microns of the optimal focus (as indicated by the upper and lower curves in each Figure converging with lines 902). FIG. 9D (8 um) indicates that an 8 um offset can initialize the instrument when the current focus deviates from the optimal focus by +/−10 um. FIGS. 9A, (2 um), 9B (4 um), and 9C (6 um) each indicate that their corresponding offsets might be able to initialize the instrument when the current focus deviates from the optimal focus by +/−10 um. While the upper and lower curves in each Figure do diverge beyond +/−5 um (indicating a poor focus prediction), directional information is available (i.e., the slopes are greater than 0). Providing poor focus predictability from about 5–10 um is workable, because that range represents coarse focusing, and once several iterations of coarse focusing have been implemented, the offset from optimal focus will converge to about +/−5 um, where the predictability is very good, enabling finer focusing to be achieved.

In flow imaging systems that include a TDI detector for which velocity needs to be determined to enable synchronization of the TDI detector with the flow velocity (e.g., system 100b of FIG. 2B), optical grating dimensions required for velocity estimations can be derived from the physical dimensions of the TDI detector. If there are 512 rows in the TDI detector, then it will be sufficient to accurately predict the scan rate to within one half of 1 in 512. Therefore, the accuracy requirements for such a TDI detector can be defined as about one in a thousand.

A velocity performance simulation is derived assuming a single optical grating with an offset of 4 um from the grating to the objects in flow. The objects pass through the system 100b in FIG. 2A at a velocity of 30,000 um/second. The simulations use Gaussian random noise with 5% standard deviation and 50 objects per second. It has been determined that imaging and collecting data from at least 16 objects is sufficient to meet the velocity accuracy requirement. Since auto focusing requires two optical gratings (one in optical path 104a and one in optical path 104c of FIG. 2B), either optical grating can be used to estimate the velocity. Theoretically, this configuration ought to reduce the requirement for 16 objects to only 8 objects, to reduce the noise of the measurements. In reality, the objects are not always optimally focused. If an object deviates from an optimal focus position by several microns, the grating closest to the object will enable a more accurate velocity estimation to be achieved. Therefore, averaging of velocity estimates can be weighted according to the estimated focus projection.

Figure 10:
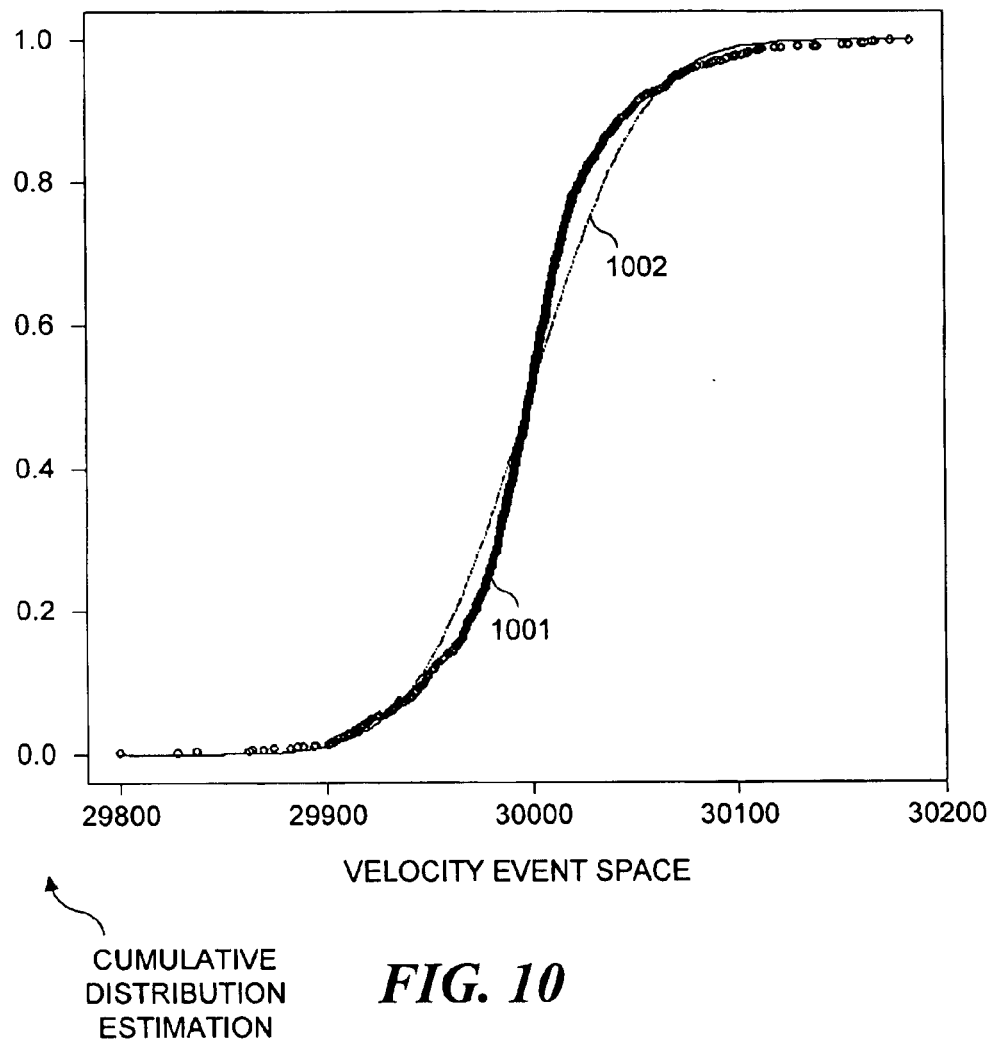
FIG. 10 is a graph of an empirical cumulative distribution function for 1000 estimates of velocity.

FIG. 10 is a graph showing an empirical cumulative distribution function (a curve 1001) for 1000 estimates of the velocity. The velocity estimates are sorted on the x-axis. The equivalent Gaussian distribution is plotted as a line 1002. The distribution of the 1000 velocity estimations suggests that the empirical cumulative distribution is different from a Gaussian distribution, with the empirical cumulative distribution being similarly symmetric, and having slightly larger tails. Significantly, the symmetry of the empirical cumulative distribution enables simple averaging to reduce the variations. Note that without averaging, many data points are well outside the 0.1% (i.e. one in one thousand) tolerance requirement defined above for a 512 channel TDI detector.

Figure 11:
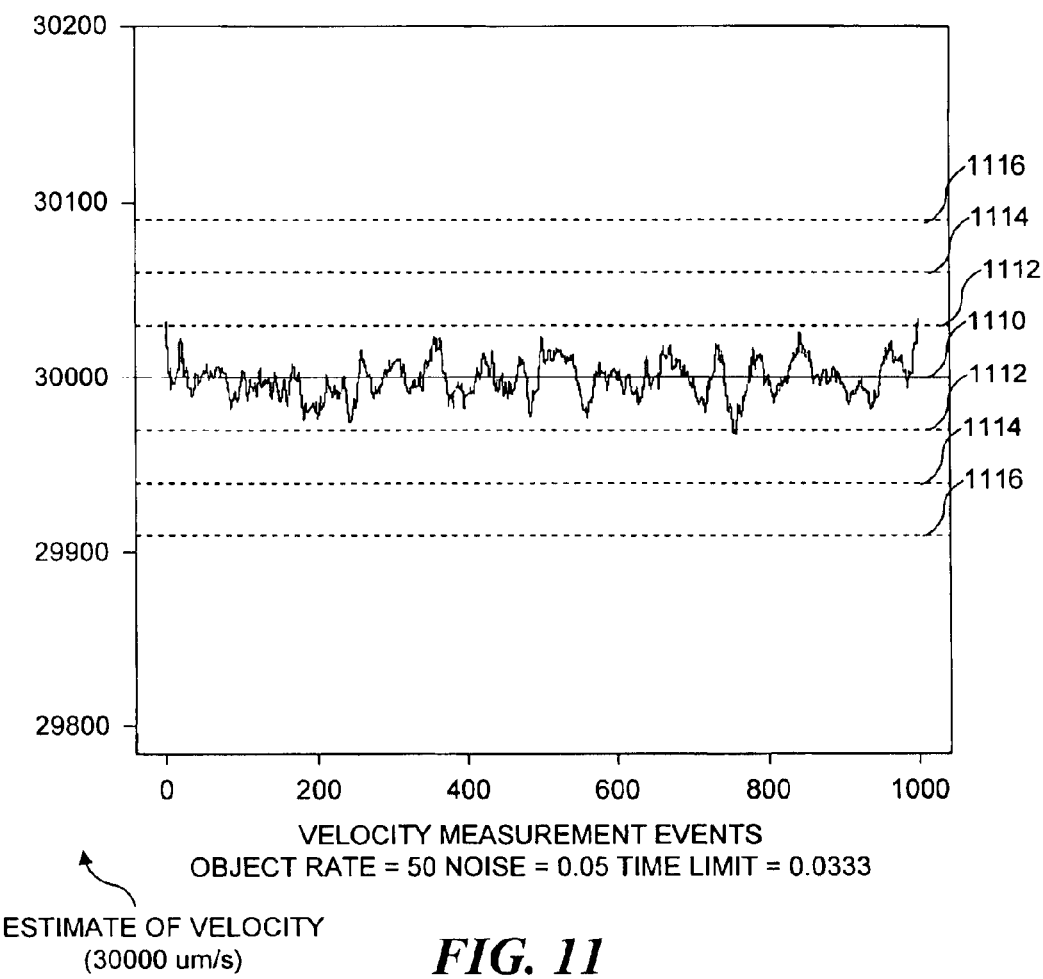
FIG. 11 is a graph showing the effects of averaging sixteen measurements with a simple Finite Impulse Response (FIR) filter.

FIG. 11 is a graph showing the effects of averaging sixteen measurements with a simple Finite Impulse Response (FIR) filter. A line 1110 corresponds to true focus, while lines 1112 define a 0.1% tolerance range, lines 1114 define a 0.2% tolerance range, and lines 1116 define a 0.3% tolerance range. With sixteen measurements, the velocity estimations are within the 0.1% tolerance requirement.

The focus function would be trivial to carry out and calibrate if the input signals were consistent. For simplicity, a basic focus function is derived below based on consistent inputs, enabling definitions and the overall scope of the problem to be described in a relatively simple context. Once the basic focus function has been discussed below, a complex focus function is derived to deal with the problem of inconsistent input signals due to inconsistent concentrations of sample objects such as beads. The inconsistent concentration impacts the ability to compute and calibrate the focus function. Next, a calibration of the focus function independent of concentration will be discussed below. A method for positioning the two optical gratings and calibrating the detector independent of concentration will then be discussed. Finally a method for initializing and calibration of an appropriate system with auto focus capability in accord with the present invention will be explained.

Focus Function from Consistent Signals

The focus function is parameterized by stage position (see stage 108 of FIGS. 2A and 2B) and the grating offsets from the focal points in each optical path. The focus function is generated by the following relationship:

$$F(z) = \frac{P(z) - M(z)}{P(z) + M(z)}$$

where P(z) and M(z) are measurements from plus and minus grating/PMT devices, respectively, at a stage position z. Referring to FIG. 2B, optical path 104a corresponds to a plus grating/PMT device, and path 104c corresponds to a minus grating/PMT device based on the positions of the optical grating relative to the focal point in each path.

Figure 12:
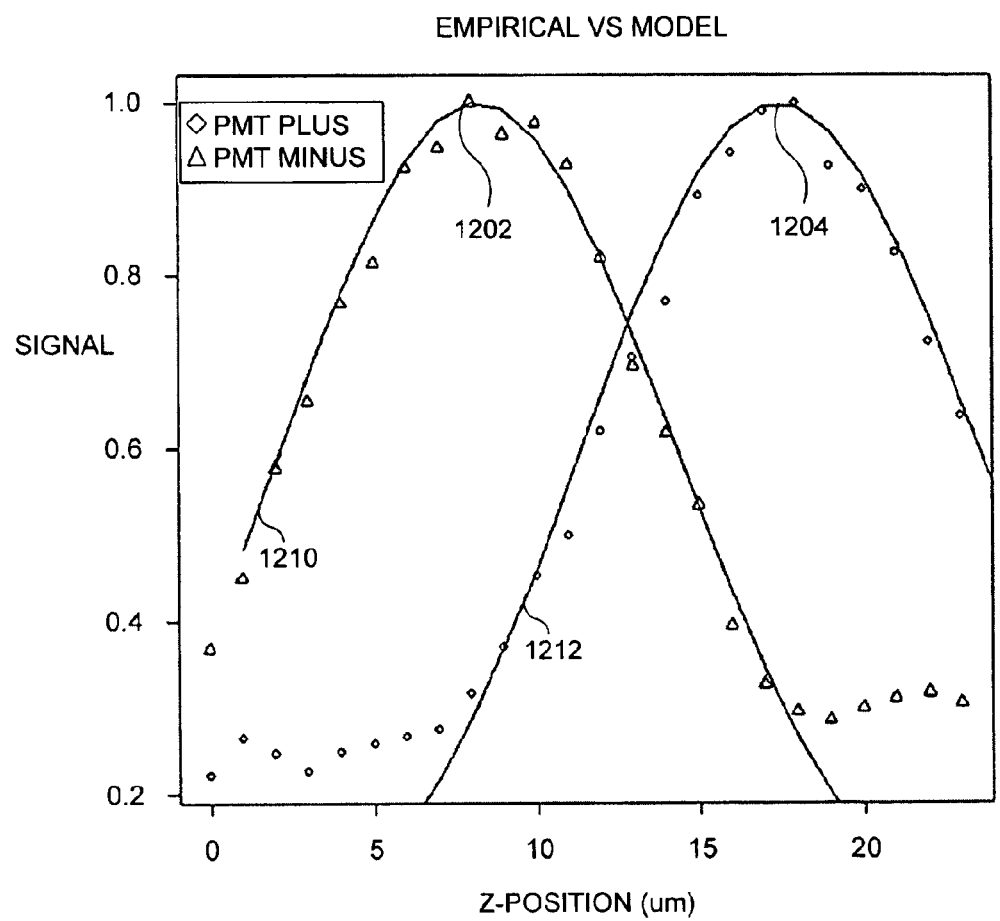
FIG. 12 is a graph showing signal data collected from first and second optical paths, where each optical path includes an optical grating and a detector, where one optical grating is disposed offset from a reference focal point in a first direction, and the other optical grating is disposed offset from the reference focal point in an opposite direction.

Modeling of the signals, P(z) and M(z), generated by the two signal devices is described in greater detail below. FIG. 12 is a graph illustrating the response of signal devices the produce signals P(z) and M(z) with respect to the stage position (i.e., the z-position, the direction of the light propagation). The diamonds and triangles indicating empirical data point in FIG. 12 correspond to a statistic derived from repeated measures of M(z) and P(z), as described in greater detail below. The empirical data were collected using a flow imaging system generally consistent with system 100b of FIG. 2B. Peaks of each signal correspond to an optimal focus.

Lines 1210 and 1212 represent Gaussian normal distribution functions fitted to such statistical data points. Each curve was fitted using two Gaussians with mean and standard deviations (SD) as follows: mean=7.25, SD=6; and mean=16.5, SD=6. The two Gaussians have the same standard deviation, which is related to the optical numerical aperture of the system, and have means that indicate a separation of 9.25 um=16.5 um (see peak 1204)−7.25 um (see peak 1202). With a separation distance of 9.25 um, each grating will be offset by 4.75 um from a reference focal point (in object space). This model will be used to address grating separation presented in a later section.

Figure 13:
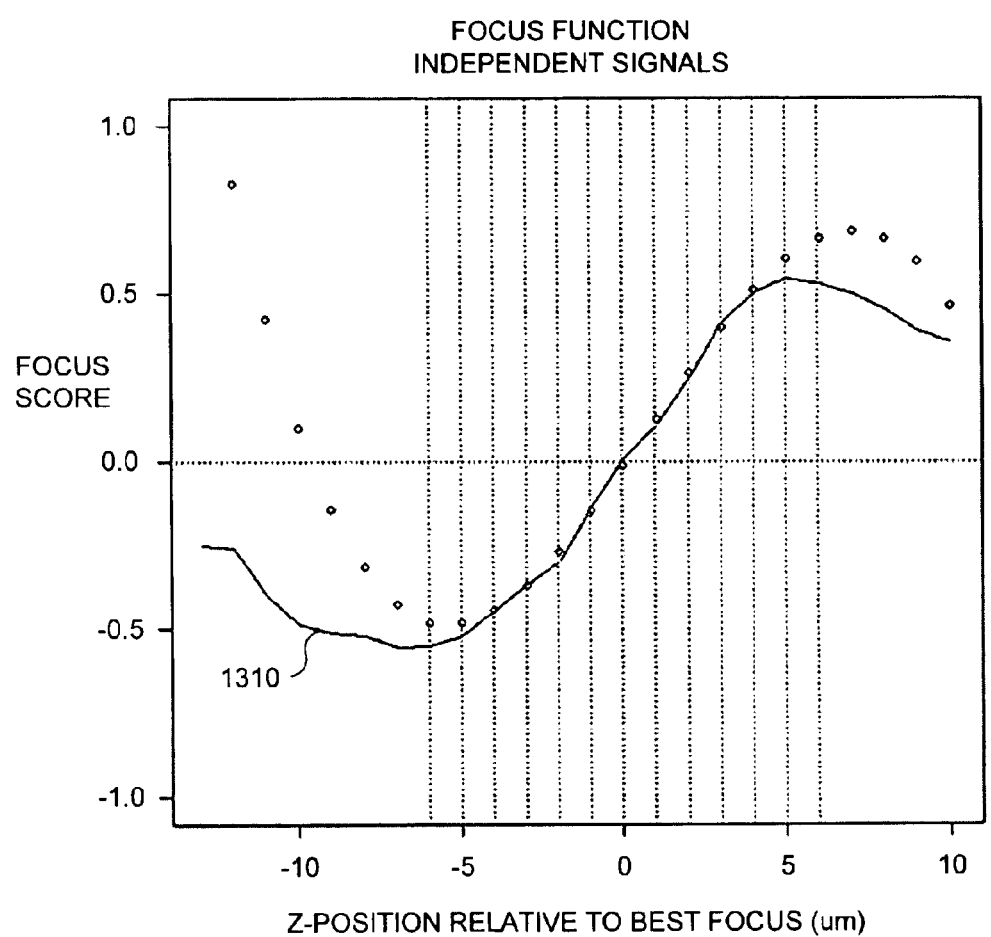
FIG. 13 is a graph showing a focus function based on the signal data from FIG. 12.

In FIG. 13, a basic focus function indicated by a line 1310 is derived from the diamonds and triangles used for the data points in FIG. 12. A third degree polynomial is used for modeling the data with the points ranging from +6 um to −6 um from the z-position corresponding to F(z)=0. The focus function sensitivity is defined as the slope at best focus, or dF(0)/dz, which can be used to calibrate one instrument's settings with another. In other words, an instrument's focusing measure should have the same sensitivity as another instrument when the core is in focus. The coefficient corresponding to the linear term is the focus sensitivity, dF(0).

Assuming consistent signal input, the curves shown in FIGS. 12 and 13 can be used to determine and calibrate the basic focus function. If the sensitivity of the focus function is not within tolerance, then the gratings providing the P(z) and M(z) signals in the devices are moved closer or further apart, and the sensitivity is once again determined. To predict the amount of spacing, the statistical data of FIG. 12 would be used, and the signals corresponding to lines 1210 and 1212 would be separated until the desired focus function sensitivity is achieved.

Focus Function from Inconsistent Signals

Figure 14:
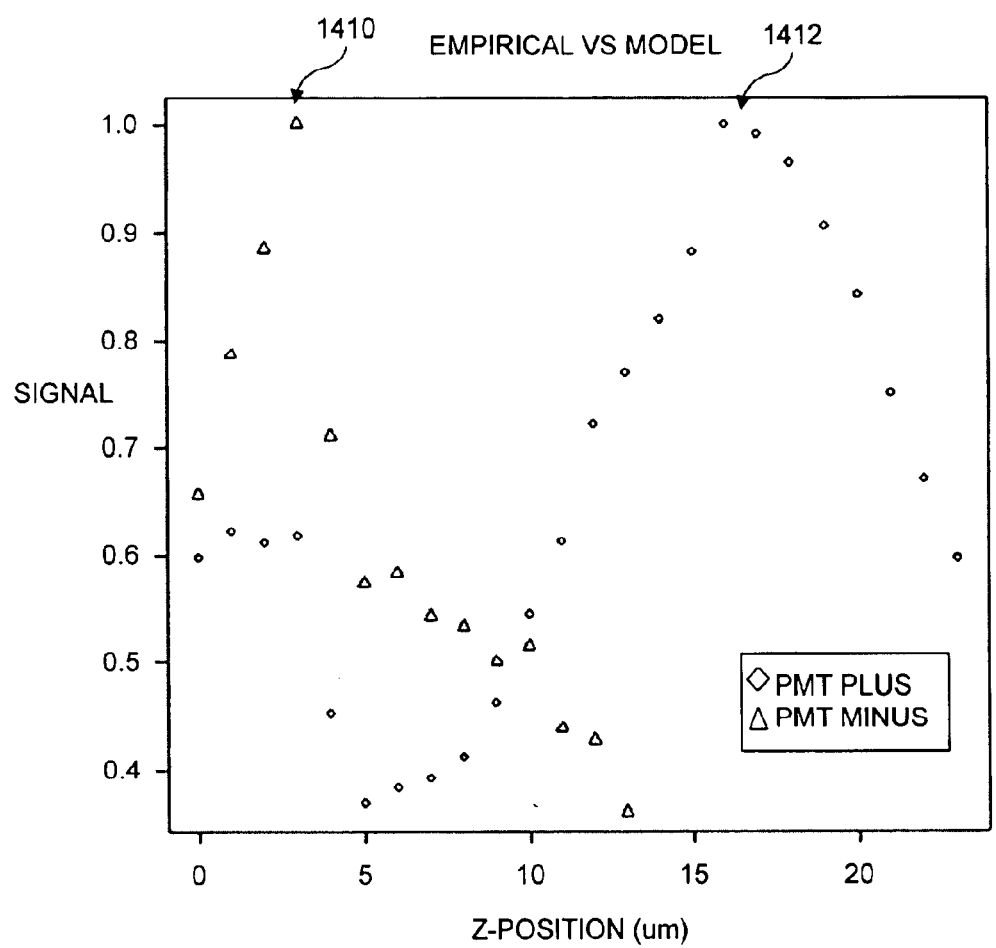
FIG. 14 is a graph showing signal data similar to that illustrated in FIG. 12, but in which a concentration of objects in flow from which the signals were generated varied.

The main cause of inconsistent signals for P(z) and M(z) is the concentration of sample objects (such as beads) in the core of the flow cell. More objects stimulating the grating signals results in a stronger signal. FIG. 14, which is similar to FIG. 12, is another graph illustrating the response of signal devices producing signals P(z) and M(z) with respect to the stage position (i.e., the z-position). Note that the signals have two peak responses, generally indicated by peak 1410 and peak 1412, because the concentration of objects was relatively high when the z-position corresponded to less than about 5 um, and became relatively low when the z-position corresponded to more than about 15 um. The confusion of the signal by concentration changes, as indicated in FIG. 14, is exemplary of the empirical data.

Figure 15A:
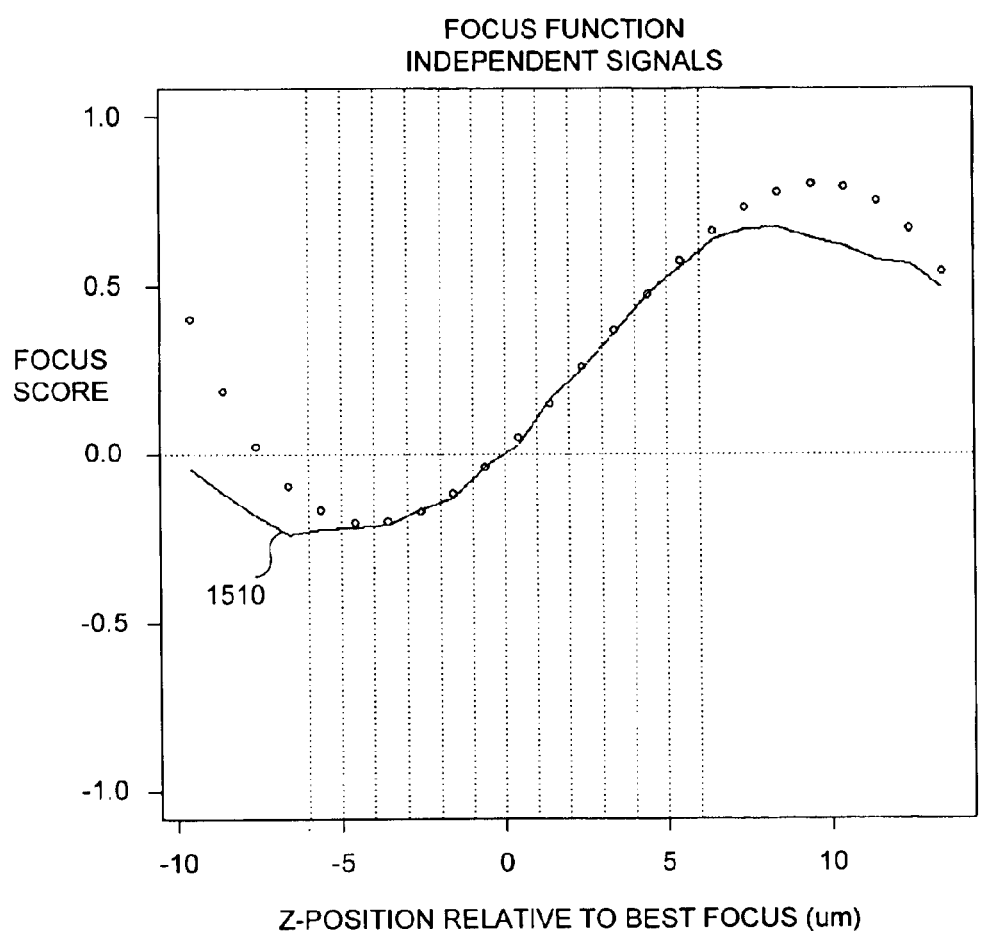
FIGS. 15A and 15B are graphs of focus functions based on the signal data from FIG. 14.
Figure 15B:
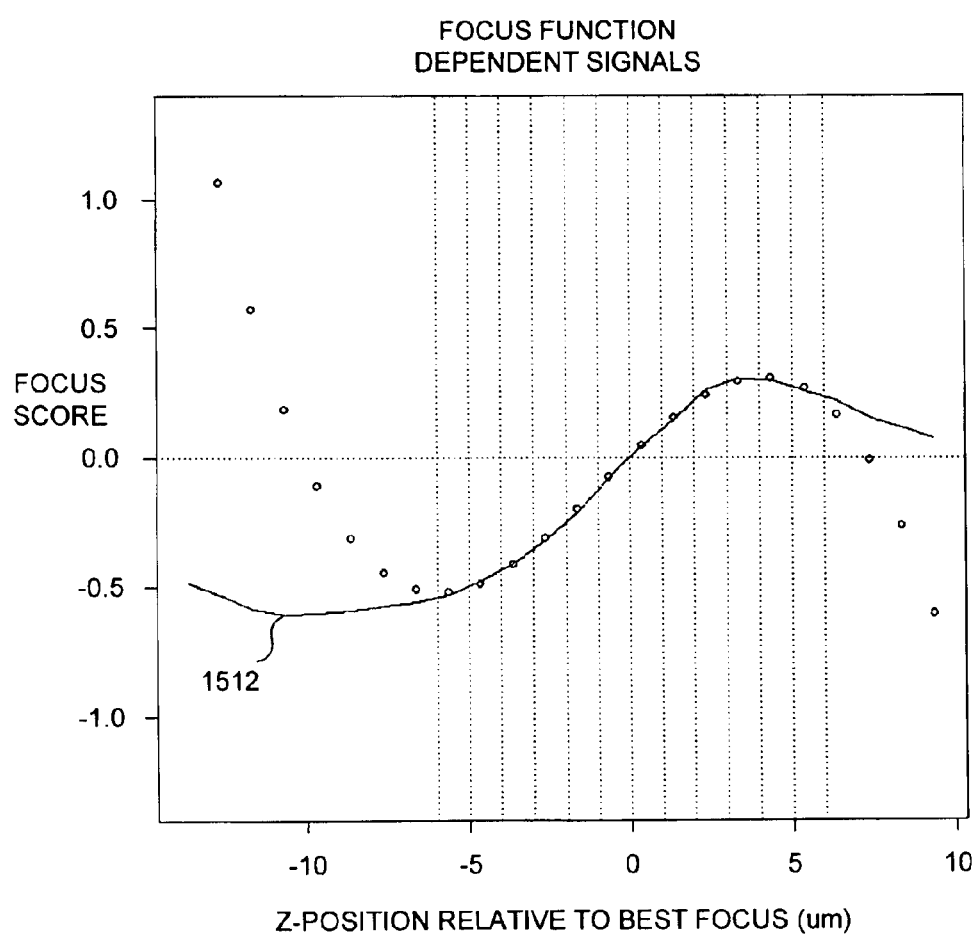

FIGS. 15A and 15B demonstrate the effect of concentration on the focus function. FIG. 15A relates to a function, exemplified by a line 1510 and derived using the signal response from the empirical model discussed above (i.e., data from a single optical grating). FIG. 15B relates to a function, exemplified by a line 1512, derived using median statistics (discussed below) from repeated measurements of the focus score at each z-position. In other words, the simultaneous signal responses from the two optical gratings are used to generate the focus score, which is the score used in the normal operation of the instrument. Each plus and minus signal is stimulated by the same beads within the core. Thus, the focus score is independent of the concentration and size of beads in the core, for FIG. 15B.

The focus sensitivity derived from independent signals is 0.09 (data from a single optical grating), versus the focus sensitivity of 0.12 derived from dependent signals (data for two optical gratings), which are significantly different. In the basic focus function discussed above, the focus sensitivity for independent signals is 0.138 (data from a single optical grating), more closely corresponding to the focus sensitivity of 0.141 for dependent signals (data for two optical gratings), which is as expected because changing concentration was not a factor in the basic focus function.

While FIG. 15B illustrates a focus function determined based on changing concentrations of sample objects, focus function 1512 of FIG. 15B cannot be calibrated so as to have similar sensitivities, because it is not possible to independently shift the plus and minus responses illustrated in FIG. 14 to derive another focus function with the proper sensitivity. Therefore, the signals from the plus and minus gratings cannot be treated independently; and in general, plots such as that shown in FIG. 14 are of little use.

The calibration of the complex focus function (changing inputs) will now be discussed, and the statistics used for computing the focus function (noted above with respect to FIG. 12) will be described. To compute the focus function, statistics are employed to deal with variations in the focus scores, which are mainly attributable to core thickness of the sample fluid in the flow cell. The core thickness yields signals that actually vary in z position (and also in lateral position). Thus, multiple measurements are taken, and the median is used. The mean of the focus scores is not used because the focus measurements are not generally distributed symmetrically. The only exception to this rule is when the stage position is exactly centered between the optical gratings. The core thickness only affects the spread of the distribution, and the main mode of the distribution should not change.

Figure 16A:
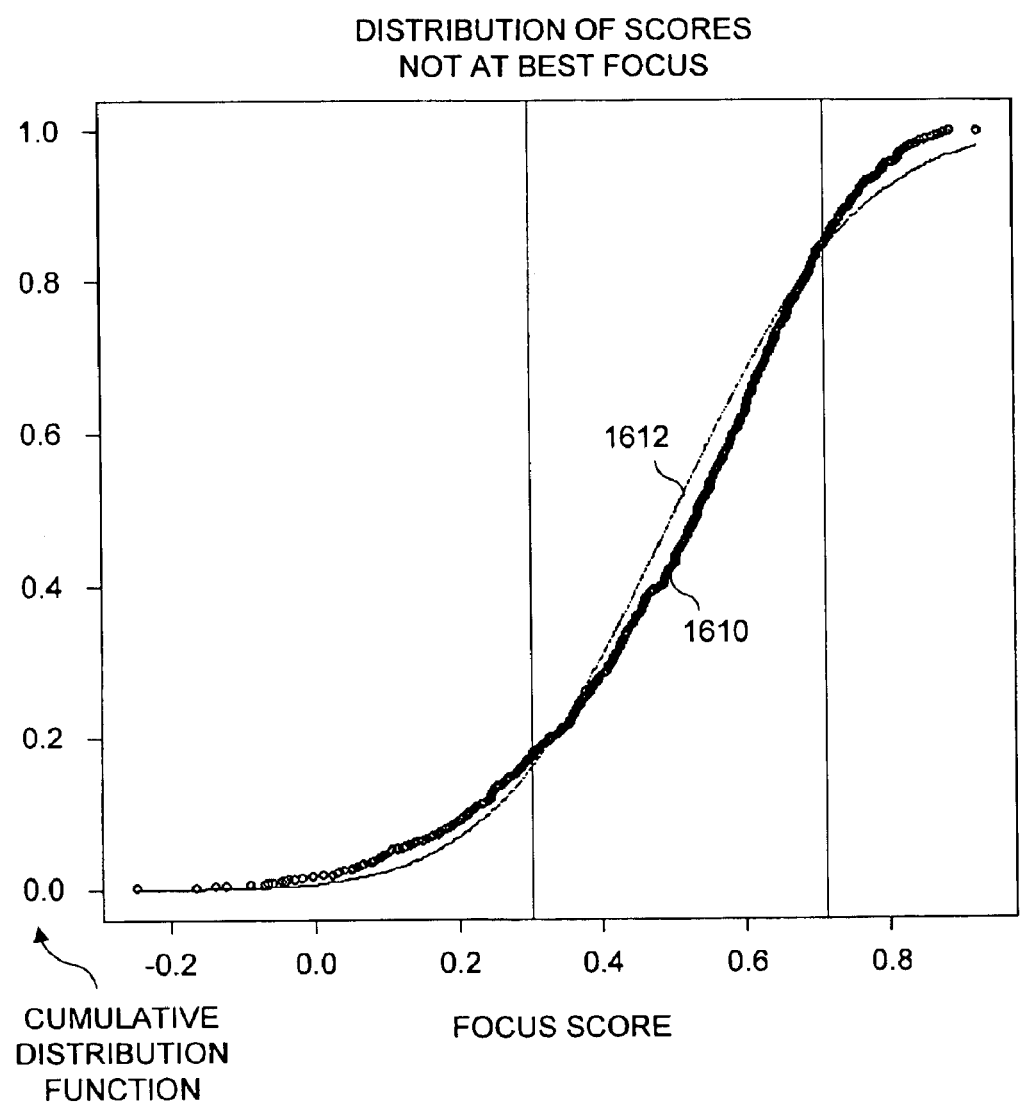
FIGS. 16A and 16B are graphs of cumulative distribution functions showing why grating offsets are preferably symmetrical.
Figure 16B:
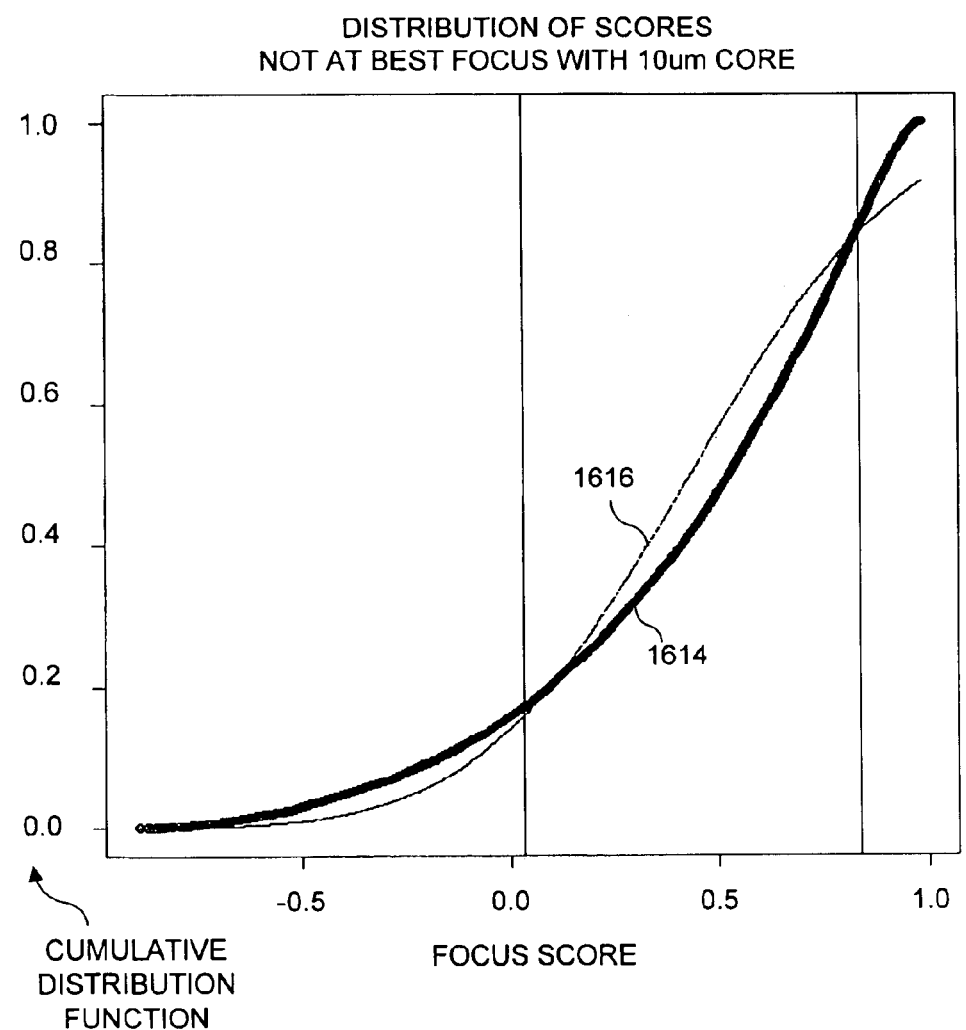

Even though an object's distribution around a z-position is symmetric (Gaussian), the signal response is not symmetric about any z-position other than zero. FIG. 16A is a graph illustrating a simulated distribution of focus scores based on gratings positioned at −3 um and 9 um (in object space) away from optimal focus and a core width of 5 um. FIG. 16B is a similar graph based on a core width of 10 um. Curve 1610 of FIG. 16A and curve 1614 of FIG. 16B are based on multiple simulations of focus score. Line 1612 of FIG. 16A and line 1616 of FIG. 16B are Gaussian distributions with the same mean and SD, which definitely demonstrates that the distribution is skewed. The mean of the data is 0.505 and the median is 0.538. The score corresponding to an object at the 3 um position is 0.534. The size of the core changes the distribution of the focus scores. To demonstrate the effect of core size, the z-position statistics are changed from 1.5 um to 3 um for SD, where 1.5 um corresponds to a 5 um core and the 3 um SD corresponds to a 10 um core. The mean of the data is 0.436, and the median is 0.531. For both core sizes, the median score corresponds to the target score.

Calibration of the Focus Function

To calibrate the focus function, a method for obtaining the correct sensitivity by properly spacing the gratings is required. One method would be to take a first best guess at the spacing using mechanical/optical tools, and then generate a focus function. If the sensitivity is higher than required, then the gratings are moved closer by some predefine amount "x." A new focus function is generated, and the sensitivity checked again. The process of moving the gratings and checking the sensitivity is repeated as required to achieve the desired result. The relationship of focus function sensitivity to grating separation is approximately linear.

An alternative method to calibrate the focus function is to characterize the signal response from the plus and minus gratings with a given optical system and components. The signal response should not change from instrument to instrument. Consequently, it ought to be possible to measure the signal response for a single instrument and use the results for all instruments of the same design. A method for calibrating the focus function based on a specific instrument design is likely to be more efficient than the repeated trials method discussed above.

Figure 17:
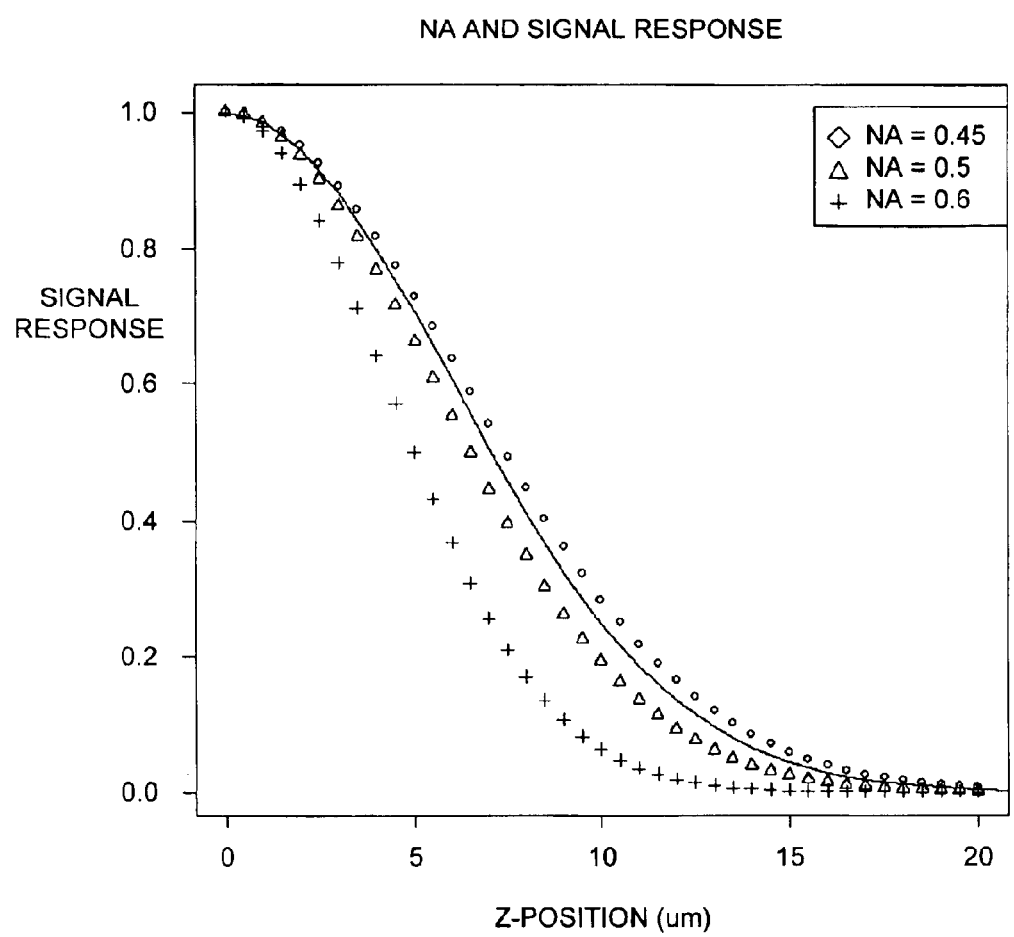
FIG. 17 is a graph of signal response versus the distance of a sample object with respect to the grating for three different numerical apertures.

FIG. 17 is a graph of signal response plots versus the distance of the sample object from the grating. Three different plots correspond to three different optical numerical apertures (NAs) are simulated and represented, including: 0.45, 0.5 and 0.6. A line 1710 represents a curve fitted to a Gaussian function with a standard deviation of 6.0, which was also used in FIG. 12. Thus, the empirical data suggests that the NA is between 0.45 and 0.5, within 8 um of focus. The system employed actually used an objective lens having a numerical aperture and a power of 40x.

Figure 18:
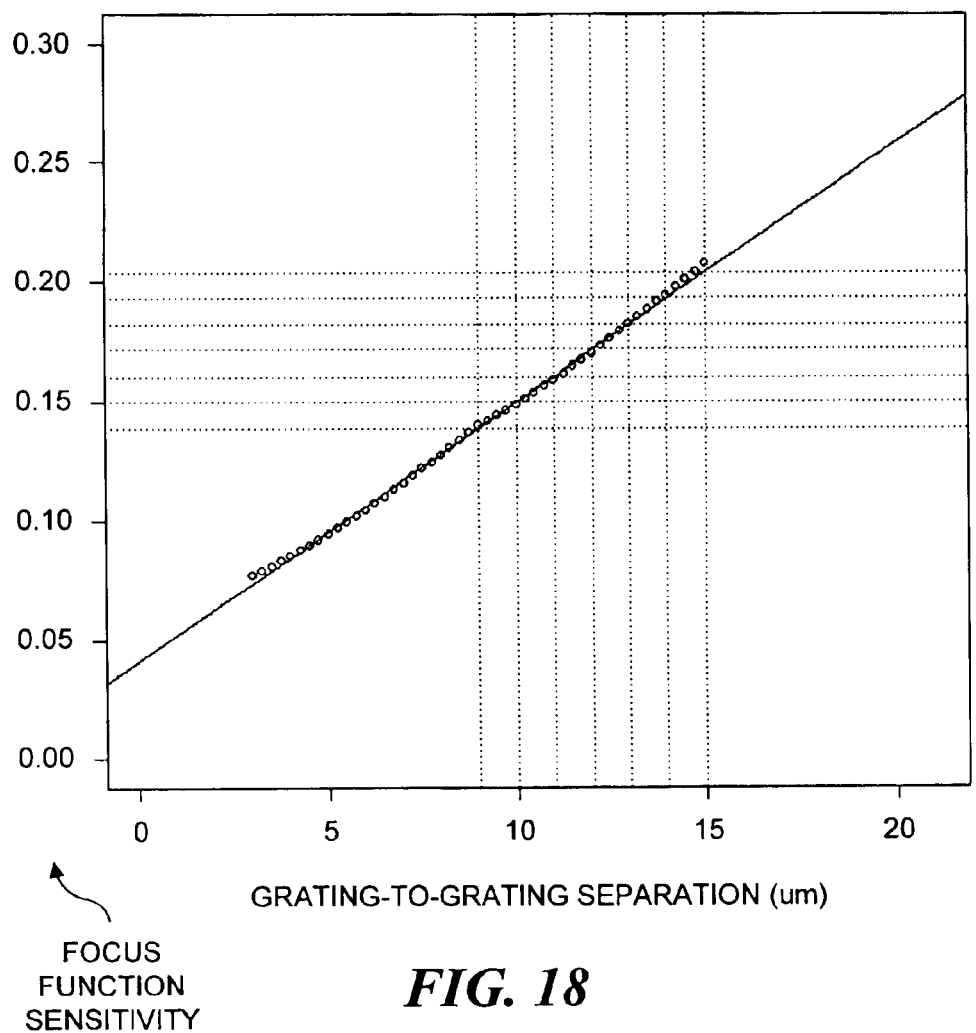
FIG. 18 is a graph showing the generally linear relationship between focus function sensitivity and grating to grating sensitivity.

Using the Gaussian function to predict signal response from each grating, the focus sensitivity can be estimated as a function of grating spacing. FIG. 18 is a graph of focus function sensitivity versus grating separation distance, derived using a SD of 6.0 for signals from each of two gratings. Clearly, the relationship between focus function sensitivity and grating-to-grating separation is linear. The intercept and slope of the line fitted to the data points are 0.04073 and 0.01087, respectively. Note that the focus sensitivity measurement for the data with constant concentration is 0.141 (the basic focus function discussed above), placing grating-to-grating separation at about 9.2 um, which corresponds well to the separation distance identified in the fit originally performed in FIG. 12 (i.e., 9.25 um). Thus, given a specific instrument design, grating spacing and the increment that should be used to re-space the gratings can be predicted.

Based on the values noted above, the target total separation distance (in object space) between two gratings is initially set to 12 um (an increase of about 30% over 9.2 um), which corresponds to a focus sensitivity of 0.171. The focus sensitivity predictions (with a linear fit), for 11 um, 12 um and 13 um separation, are: 0.160, 0.171, and 0.182, respectively. It is recommended that the tolerance for focus sensitivity setup should range from about 0.16 to 0.182. According to the separation function, the constant concentration data indicate that the optical gratings must be spaced 2.8 um further apart in this example.

Calibration of Initial Grating Position and Detector Signal Gain

Due to concentration inconsistencies in the signal input, the initial position of the optical gratings and detector gains must be performed with signals that are independent of the concentration. To initially position the optical gratings in optical paths 104a and 104b of FIG. 2A (or optical paths 104a and 104c of FIG. 2B), as necessary to achieve the optimal focus, the gratings must be moved manually so that the primary collection lens of the flow imaging system (i.e., lens 110 of FIGS. 2A and 2B) is focused at the middle of flow cell 106 (and more specifically, at the middle of a core sample fluid flowing through the flow cell, which under most circumstances, will be positioned in the middle of the flow cell. Statistically (i.e., using the mean or median), the signals generated using light modulated by the optical gratings will exhibit peak intensity when the primary collection lens of the flow imaging system is focused on the middle of the core. At this stage of calibration, the detector gains are set to a nominal value. Each optical grating is moved until the contrast identified by the corresponding detector is at a maximum. The signal that is used must be concentration independent, since this calibration step is not immune to concentration changes.

It is recommended that the signal to be used in the calibration of signal P (i.e. the signal from detector 130) be:

$$\frac{P(z)}{M(z)}$$

Similarly, it is recommended that the signal to be used in the calibration of signal M (i.e., the signal from detector 138) be:

$$\frac{M(z)}{P(z)}$$

If the calibration is for the signal from detector 130 (i.e. the optical path with the "plus" or "P" offset), then only optical grating 126 (i.e., the P grating) is moved, and grating 134 (i.e., the optical grating in the optical path with the "minus" or "M" offset) is held in the same position, as is lens 110 (i.e., the primary collection lens), relative to its z-position. Similarly, if the calibration is for the signal from detector 138 (i.e., the optical path with the "minus" or "M" offset), then only grating 134 (i.e., the M optical grating) is moved, and optical grating 126 (i.e., the optical grating in the optical path with the "plus" or "P" offset) is held in the same position, as is lens 110, in regard to its z-position.

Detector Gain Settings

Once the gratings are initially positioned, the detector gains can be set. Detector gains are set so that each detector will exhibit the same response for a given input, and so that signals provided by each detector are not saturated. The procedure to set the gain of a detector is as follows:

Either detector P or detector M (i.e. detector 130 or detector 138) is selected and its gain is set at a percentage of the total range of the analog to digital converter (ADC) for the detector. The ADC voltage range is from +/−R. The average of the absolute peak intensity is set to a percentage of R, preferably, from about 40% to about 60% of R.

Next, the other detector is adjusted such that the average focus score S(z) is within 0.01 of zero. The focus score is normalized such that 0.01 within zero is the same as the difference between the signals should be if within 1% of the total of the signals.

Summary of Setup and Calibration

Auto focus and speed setup involve taking measurements from two identical devices (i.e., optical paths 104a and 104b of FIG. 2A or optical paths 104a and 104c of FIG. 2B) that generate signals used for both auto focusing and velocity estimation (e.g., to enable a TDI detector to be synchronized with a fluid flow). Note that auto focusing can be performed independently of velocity detection. Since the focus score relies on the balance of information from the detectors in each optical path, the elements in each optical path must be setup to produce signals that are balanced with each other. The elements in each optical path include optical gratings and detectors.

There are two goals for the setup of the optical gratings. Each optical grating should be initially positioned so that best focus is in the middle of the range of stage motion, which ensures that optimal focus is not setup near the limits of stage motion. The separation distance between opposed optical gratings yields a focus function whose sensitivity is within a certain range at optimal focus.

With respect to the detectors (preferably implemented as PMTs), the PMT gains should be calibrated such that the signal strength of each PMT is equivalent for an identical signal. The PMT gain is a function of optical grating position relative to optimal focus. Therefore, the setup of PMT gains is a two-step process. The first step is to ensure that each optical path is receiving the same signal. Each optical path must be setup to achieve optimal focus. For each optical path, the PMT gain is set to a nominal setting. The corresponding optical grating is positioned at best focus using optical tools, employing a first guess at the best focus position. Then, in the second step, concentration independent measurements of contrast strength are made and the optical grating is moved relative to optimal focus and the peak contrast strength. The peak contrast strength occurs at the best focus position for the optical grating relative to the core.

After the first step is performed for each optical path, the second step ensures the PMT gains do not saturate the signals. Since each optical path is receiving the same signal, it is recommended F(z) (discussed above) be used as the measure for calibration.

At this point, the optical gratings and detectors (PMTs) have been matched to achieve optimal focus and gain. The next step is to separate the optical gratings to achieve a focus function whose sensitivity is within a certain range at optimal focus. Given the optical NA of the system and the response of contrast versus grating separation, focus sensitivity is determinable as a linear function of the separation. Therefore, an initial separation and measurement of focus sensitivity will indicate the actual separation. If the sensitivity is not within the tolerance, using the data of FIG. 18 and the initial measurement of focus sensitivity, the amount of separation that will be required can be determined. Also, the z-position of the zero crossing of the focus function will indicate how the two gratings should be moved so the focus stage system is at the center of its travel.

Initial Grating Positioning in a Particularly Preferred Imaging System

Referring to FIGS. 2A and 2B, a particularly preferred imaging system employs petzval lens sets for focusing lenses 124 and 132. When such a preferred system is first aligned, each f=50 mm petzval set focuses the image of the field stop upon its respective grating. This is achieved by viewing a focused image of either the back or front side of the grating (preferably by using a cemented doublet, and an electronic autocollimator), and moving the petzval set until the image of the field stop can be seen clearly in focus in the deep red wavelengths. When both images are in focus, it can be concluded that an image of object 102, projected on the plane of the field stop, will also be in focus on the grating.

The auto focus system cannot function before spacing the two f=50 mm petzval sets, so when an object is imaged before such spacing occurs, the images in each optical path (i.e. optical paths 104a and 104b of FIG. 2A, and optical paths 104a and 104c of FIG. 2B) may or may not be in focus on the field stop. Nonetheless, variations in signal strength due to changes in focus from object to object (when a flow of objects is introduced into flow cell 106) should affect both detectors 130 and 138 equally, as they gather light from identically focused paths. Prior to spacing the gratings, detector gains are independently adjusted to match the signal strength (a DC peak voltage measurement). If detectors 130 and 138 are employed in conjunction with an amplifier, then amplifier gains are adjusted to match the strengths of the post-amplifier signals.

Matching the signal strengths in this fashion compensates for differences in detector and amplifier gains, as well as for any difference between the amount of light sent down each path by the 50/50 beam splitter (i.e. beam splitter 112 for FIG. 2A and beam splitter 122 for FIG. 2B). Each of these factors will affect signal strength, and only by properly balancing them can the ratio of detector signals be accurately related to the relative focus of images on each grating.

Once the signals are balanced, the two f=50 mm petzval sets are moved equal but opposite axial distances relative to each grating. This is achieved by pushing the lens mounts against a block that has been set the proper distance away from the mount prior to the first (equal) alignment of the petzval sets.

Once this spacing is complete, one petzval set projects an image just in front of its grating, while the other projects an image just behind its grating. Both field stop images are separated by equal but opposite axial distance from their gratings, giving equally defocused images on each grating. Both detector signals are now the same strength when the system is at best focus on the detector 120 (FIG. 2B), and defocused on the gratings, and each detector gives the same signal strength when its image is focused on its grating.

Real Data Analysis

Empirical data have been collected from an instrument that is generally consistent with system 100b of FIG. 2A. Initial system settings were:

20.34 um pitch grating;

32 mm/sec flow speed;

6 um sample objects (as well as objects of other sizes); and

300 Hz /10 KHz, 6 dB band pass filter.

Figure 19:
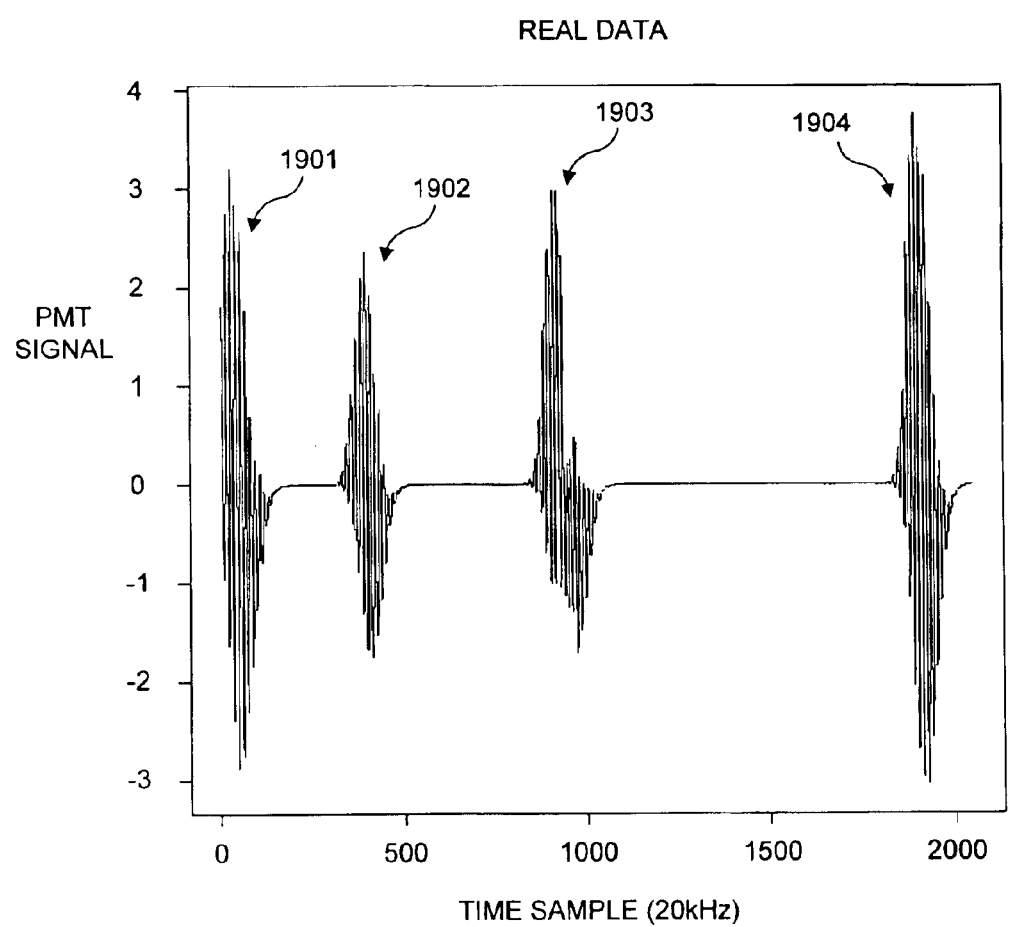
FIG. 19 is a graph of empirical data from a flow imaging system including four separate events.

FIG. 19 graphically illustrates the first 2048 samples of data captured, showing four separate events 1901–1904. Event 1903 appears to be two beads exciting the PMT simultaneously.

Figure 20A:
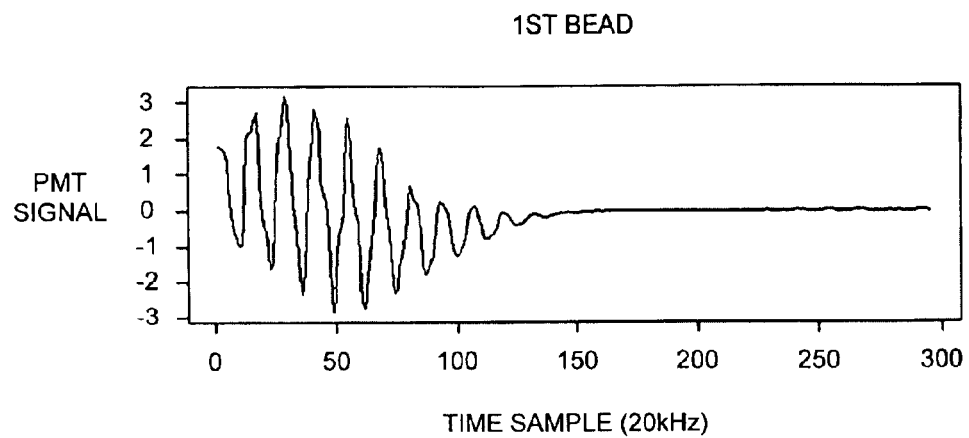
FIGS. 20A–20C are graphs showing details corresponding to the first, second and third events of FIG. 19.
Figure 20B:
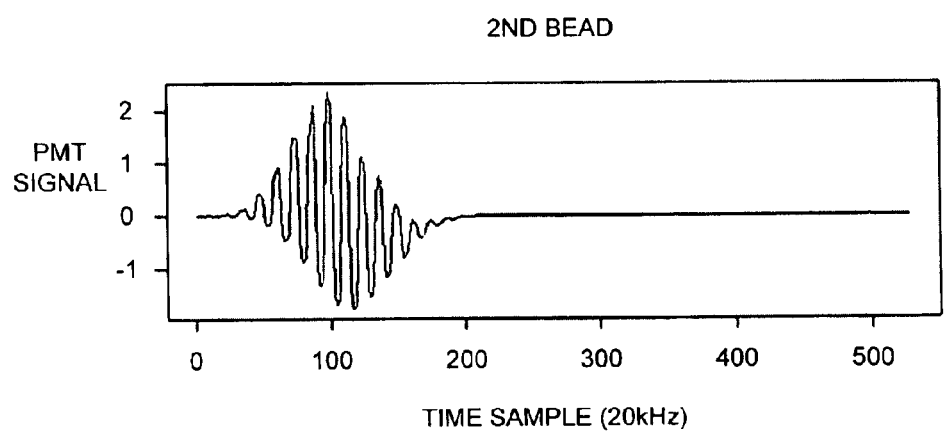
Figure 20C:
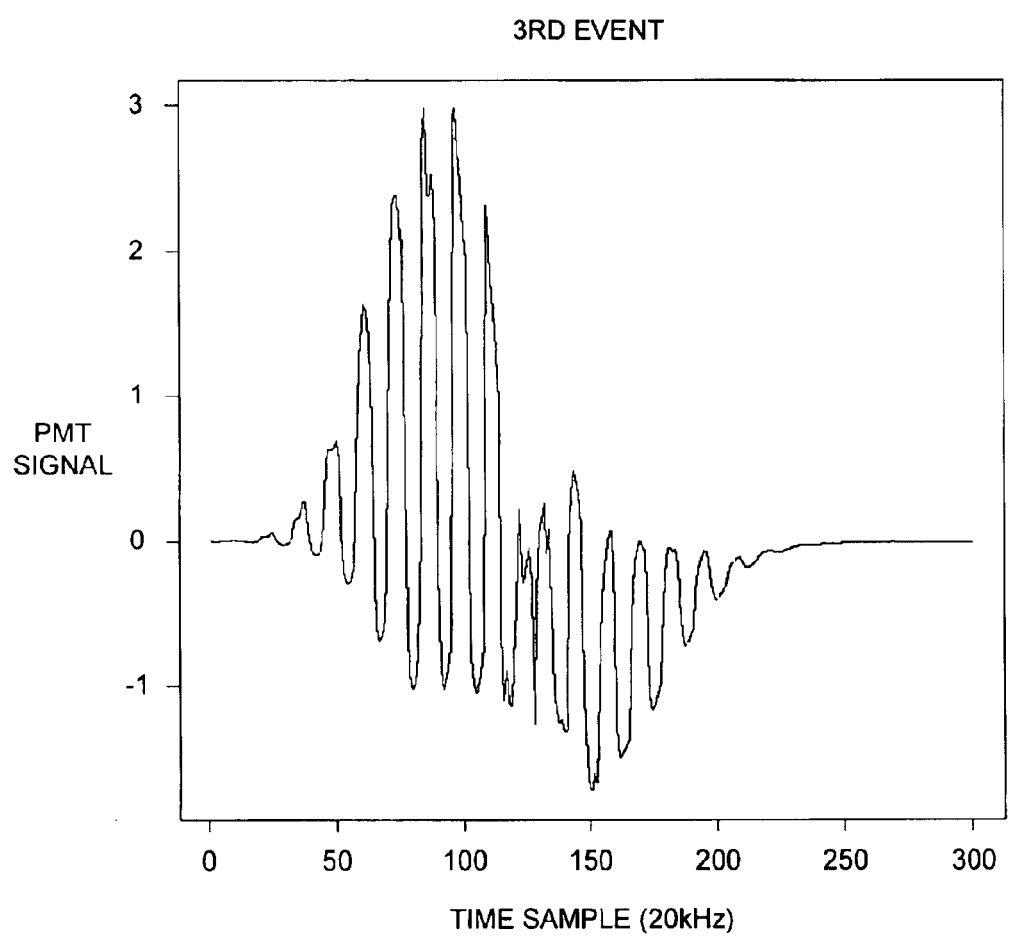

FIG. 20A graphically illustrates data corresponding to event 1901 (a first bead). FIG. 20B graphically illustrates data corresponding to event 1902 (a second bead). FIG. 20C graphically illustrates data corresponding to event 1903. Event 1903 appears to include both third and fourth beads in the data collection envelope. There are high frequency artifacts at some of the peaks and low points of the oscillation. It is speculated that the beads do not appear as disks, but as two half-moons facing each other.

Figure 21A:
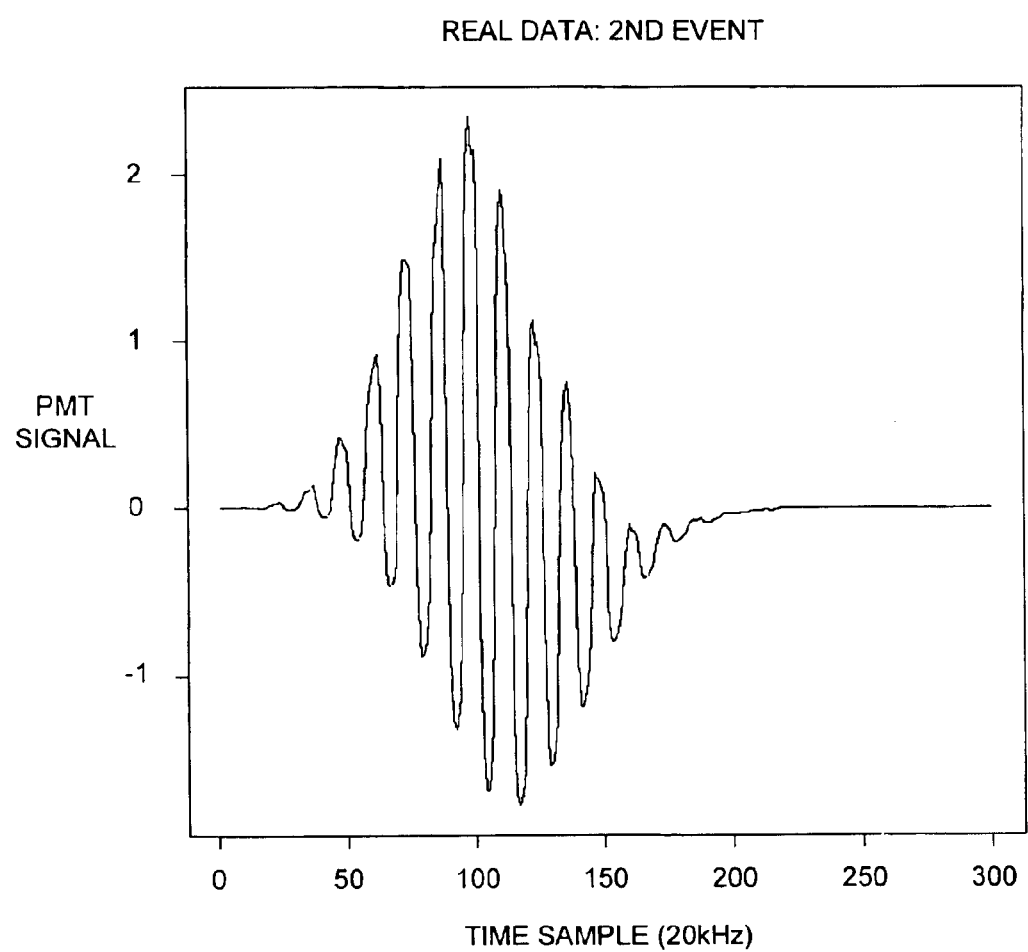
FIGS. 21A and 21B are graphs showing details corresponding to the second events of FIG. 19.
Figure 21B:
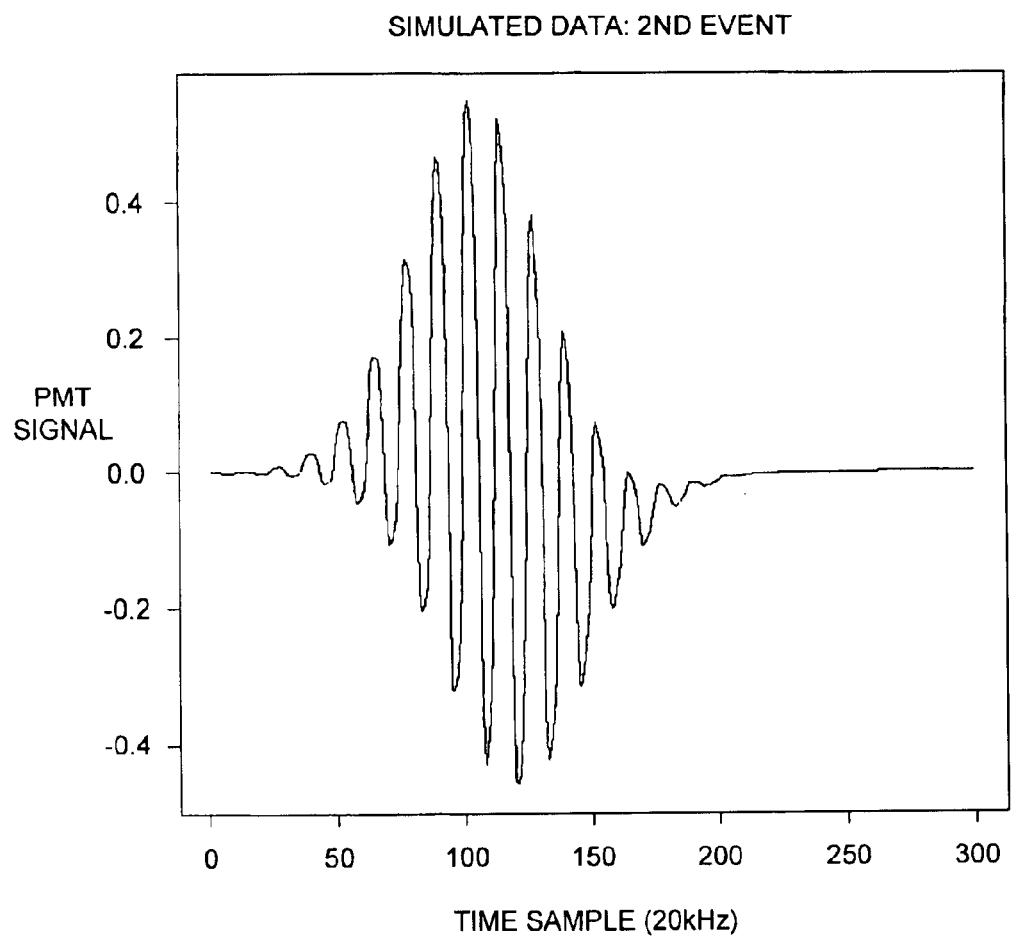

In order to verify simulations, an attempt was made to simulate the second event of one whole bead entering and exiting the PMT excitation region. FIG. 21A graphically presents real data, while FIG. 21B graphically presents simulated data. The simulated data are based on:

a 20.34 um pitch grating;

a 720 um long Gaussian envelope;

a 32319 um/second velocity;

a bead 6 um in diameter; and a single pole high pass filter at 10 Hz.

With the dimensions of the grating pitch (20.34 um) and the sampling rate (20 KHz), measurements of velocity were made from the first hundred events. FIG. 22 graphically illustrates a cumulative distribution function (CDF) of the first hundred measurements. Note data points 2201, 2202, and 2203 correspond to measurements below 30000 um/sec. These data points are a phenomenon of the PMT.

After the above data collection and analysis, the velocity estimates were recalculated using a search algorithm to refine the estimates. Basically, an iteration of the estimate was done until convergence was detected. The recalculation is based on a distribution from 800 events.

FIG. 23A graphically illustrates the recalculation. The SD is 440, which is high. For comparison, FIG. 23B graphically illustrates a distribution with a noise level at 0.01 and 50 objects per second, resulting in a SD that is less than half (198). The tails in the graph are most likely due to the objects entering the envelope at the same time. The simulation (FIG. 23A) does not represent the population observed. Therefore, the distribution that results from real data must have another random component (other than random noise and multiple objects in the detection envelope).

To measure the other component, random noise and multiple objects in the envelope were removed. Two beads passing through the system close in time are analyzed, as graphically illustrated in FIG. 24. These beads are sufficiently close to each other that they should have the same velocity. The beads are separated by 500 samples or 500/ 20000 seconds. The velocities that are estimated from these two pulses, however, are quite different. FIG. 25 graphically displays the fundamental of the two beads. The measured velocities for the large and small signals are 32817 um/second and 31943 um/second, respectively. There is an 874 um/second difference, which is over 2.5%. This difference is most likely the main cause of the high variance in the measured velocity from real data. The difference in velocities is likely attributable to the positions of the beads within the core.

Velocity Estimation in a Two Optical Grating System

As discussed above, methods for computing velocity using optical gratings are disclosed in commonly owned and assigned U.S. Pat. Nos. 6,532,061 and 6,507,391, both entitled "MEASURING THE VELOCITY OF SMALL MOVING OBJECTS SUCH AS CELLS." The methods and apparatus described therein are based on using one optical path with an optical grating and a detector for velocity detection. In the present invention, two optical paths, each including an optical grating and a detector, are employed for auto focusing. Either optical path or both could be employed for velocity detection, so that some averaging of signals from each detector employed in auto focusing contributes to velocity detection. The velocity measurement obtained from the plus grating is Vp, and the velocity measurement obtained from the minus grating is Vm. A new velocity is defined by:

$$V = \frac{Vp*P + Vm*M}{P + M}.$$

where P and M are the focus signal measurements from their respective plus and minus optical gratings. Therefore, V favors the estimate with the stronger focus signal measurement.

Preferred Focus and Velocity Design Considerations of Bead Size and Grating Size Preferred design parameters are as follows:

1. Coarse focus measurements when out of focus up to +/−10 um, which will be adequate to focus objects with cores sizes of up to 20 um;
2. Reliable focus measurements when in focus; and
3. Reliable velocity measurements in or out of best focus. For instance, a preferred system is better than 1 (detector row) part in 512 (total detector rows), or the images will be vertically blurred by more than one pixel.

The field of view, numerical aperture of the optics and the relative bead to optical grating size affect the requirements listed above as follows. The field of view, which is fixed to be proportional to that of the detector's field of view (i.e., detector 120 of FIG. 2B), determines the number of line pairs of the optical grating that the bead will cross. The field-of-view of the detectors measuring velocity and focus must correspond to the field-of-view of the TDI detector. The more line pairs in the field-of-view, the more accurate will be the measurement of the velocity signal. However, the trade-off will be that of focus performance, which is addressed below. Thus, more line pairs will positively effect requirement 3, but will negatively affect requirements 1 and 2.

The optical NA is not determined by the focus/velocity sub-system. Higher NA values will compromise requirement 1, but are beneficial, particularly for instruments used to measure small objects such as biological cells.

The relative bead to optical grating size affects the amount of modulation, which is the product of the beads passing by the optical gratings. The larger the bead relative to the optical grating pitch, the smaller the focus signal measurements, P and M become. The trade-off mentioned above compromises the focus signal. Thus, requirement 2 is affected (see the discussion of the Contrast vs. Defocus Distance graphs discussed in detail above).

In summary, the field of view and NA of the optics in a flow imaging system (e.g., as shown in FIG. 2B) are driven by the image collection system. For a given field of view, a higher grating frequency is desired for more accurate velocity measurements. However, the higher grating frequency demands a smaller optical grating bar width, which results in a reduction in modulation strength for the focus system, since the optical grating bar width is decreased relative to the size of the bead image.

Referring now to FIG. 26, which is a flow diagram of the logical steps implemented in auto focusing in accord with the present invention, in a block 2602, objects are introduced into a flow imaging system. It should be understood that the present invention can also be utilized for objects whose positions are fixed, if the imaging system is moved relative to the objects. Yet another alternative implementation involves objects fixed to a slide, where the slide is moved relative to a fixed imaging system. In a block 2604, signals are obtained from the two offset optical gratings, as discussed in detail above. In an optional block 2606, one or more of the signals is used to determine a velocity, which can be used in an optional block 2608 to synchronize a TDI detector to the relative motion. It should be understood that while the steps represented in blocks 2606 and 2608 are executed in a particularly preferred embedment of the present invention (e.g., in system 100*b* of FIG. 2B), velocity detection, TDI synchronization, and TDI detectors are not required for the present invention (as shown for example, in system 100*a* of FIG. 2A).

In a block 2610, the signals from the paired offset optical gratings are processed to identify a direction in which a primary collection lens (e.g., lens 110 of FIGS. 2A and 2B) should be moved to improve the focus. In a decision block 2612, the logic determines if such a direction can be identified. If not (for example, when the system is already at the optimal focus, or when the components have not initially been positioned correctly, as discussed above), the logic loops to block 2604, and additional signals are obtained. If a direction is identified in decision block 2612, then in a block 2614, the primary collection lens is moved a predetermined distance in the identified direction. The logic then returns to block 2604, and the process repeats for as long as the system is operational.

With respect to moving the primary collection lens (see lens 110 in FIGS. 2A and 2B), the movements are preferably made in very small increments. The specific structure employed to move the primary lens is not significant. Indeed, the flow cell could be moved in place of the primary lens; however, movement of the flow cell could negatively impact the sheath fluid and core fluid flows in a hydrodynamically focused flow cell, and thus, movement of the primary collection lens is preferred. One simply configuration for moving lens 110 would be to attach lens 110 to stage 108 (i.e., through a support structure), and to drivingly couple the stage to a prime mover (such as an electrical stepping motor). The prime mover is controllably connected to controller 107 (shown in FIGS. 2A and 2B, where stage 108 includes a prime mover—not separately shown). In a particularly preferred embodiment, the primary optical element is attached to a flexure pate which is displaced using a micrometer driven by a stepper motor. In one embodiment, after the appropriate direction has been identified, the prime mover moves stage 108 in that direction by the smallest incremental distance that can be achieved by the movable stage. In a particularly preferred embodiment, once the focus function is determined and the direction to move the primary optical element is identified, the distance to automatically move the primary optical element is determined by a look up table.

Although the present invention has been described in connection with the preferred form of practicing it and modifications thereto, those of ordinary skill in the art will understand that many other modifications can be made to this invention within the scope of the claims that follow. Accordingly, it is not intended that the scope of the invention in any way be limited by the above description, but instead be determined entirely by reference to the claims that follow.

The invention in which an exclusive right is claimed is defined by the following:

1. A focusing system configured to focus on an object in a field of view, while there is a relative motion between the object and the focusing system, comprising:
 (a) a primary optical element disposed to direct light traveling from an object passing through the field of view along a collection path, the primary optical element being selectively positionable;
 (b) at least one beam splitter disposed to direct light that has traveled from an object and through the primary optical element along both a first optical path and a second optical path;
 (c) a first optical grating disposed in the first optical path, the first optical grating modulating the light traveling along the first optical path to produce first modulated light having a modulation frequency proportional to a velocity of the object passing through the field of view;
 (d) a first light sensitive detector on which the first modulated light is incident, the first light sensitive detector producing a first electrical signal responsive to the first modulated light;
 (e) a second optical grating disposed in the second optical path, the second optical grating modulating the light traveling along the second optical path to produce second modulated light having a modulation frequency proportional to the velocity of the object passing through the field of view, the second optical grating being disposed such that light traveling from the primary optical element to the second optical grating must travel farther than light traveling from the primary optical element to the first optical grating;
 (f) a second light sensitive detector on which the second modulated light is incident, the second light sensitive detector producing a second electrical signal responsive to the second modulated light; and
 (g) a processor for processing the first electrical signal and the second electrical signal to determine a direction along which the primary optical element should be moved to improve a coincidence between a focal point of the primary optical element and the object.

2. The focusing system of claim 1, wherein if relative positions of the first optical grating, the second optical grating, and the focal point of the primary optical element are represented in object space, the focal point is disposed between and equidistant from the first optical grating and the second optical grating.

3. The focusing system of claim 1, wherein the processor comprises an application specific integrated circuit.

4. The focusing system of claim 1, wherein the processor comprises a programmable computing device.

5. The focusing system of claim 1, wherein the first light sensitive detector and the second light sensitive detector each comprises a photomultiplier tube.

6. The focusing system of claim 1, wherein each optical path receives an equivalent amount of light from the object.

7. The focusing system of claim 1, further comprising a prime mover drivingly coupled to the primary optical element, and controlled by the processor to move the primary optical element so as to improve the coincidence of the focal point of the primary optical element and the object.

8. The focusing system of claim 7, further comprising a memory in which machine instructions and data are stored, and wherein the processor is coupled to the memory, the processor executing the machine instructions to carry out a plurality of operations, including:
 (a) after processing the first electrical signal and the second electrical signal detector signal to determine a direction the primary optical element should be moved, activating the prime mover to move the primary optical element to a new position in the direction so determined, by a predefined amount; and
 (b) processing the first electrical signal and the second electrical signal detector signal based on the new position of the primary optical element to determine a direction the primary optical element should next be moved to further improve the coincidence between the focal point of the primary optical element and the object; and
 (c) periodically repeating operations (a) and (b).

9. The focusing system of claim 8, wherein the machine instructions further cause the processor to manipulate at least one of the first electrical signal and the second electrical signal to determine an indication of the velocity of the object relative to the primary optical element.

10. The focusing system of claim 1, further comprising a memory in which machine instructions and data are stored, and wherein the processor is coupled to the memory, the processor executing the machine instructions to carry out a plurality of operations, including:
 (a) determine a focus signal measurement for the first electrical signal;
 (b) determine a focus signal measurement for the second electrical signal;
 (c) determine the velocity of the object relative to the focusing system based on the first electrical signal;
 (d) determine the velocity of the object relative to the focusing system based on the second electrical signal; and
 (e) determine the velocity of the object relative to the focusing system based on the focus signal measurement for the first electrical signal, the focus signal measurement for the second electrical signal, the velocity of the object relative to the focusing system as determined based on the first electrical signal, and the velocity of the object relative to the focusing system as determined based on the second electrical signal.

11. The focusing system of claim 9, further comprising at least one additional light sensitive detector disposed to receive the light traveling along the collection path that is not modulated by either the first optical grating or the second optical grating, and which is employed to determine a characteristic of the object.

12. The focusing system of claim 11, wherein the least one additional light sensitive detector is a time delay integration (TDI) detector logically coupled to the processor, and wherein the processor uses the indication of the velocity of the object to synchronize the TDI detector to the relative motion of the object.

13. An imaging system including an auto focusing capability, employed to image an object where there is relative movement between the object and the imaging system, comprising:

(a) a primary optical element disposed to direct light from the object along a first collection path, the primary optical element being selectively positionable;

(b) a prime mover drivingly coupled with the primary optical element to selectively move the primary optical element relative to the object;

(c) splitter means disposed in the collection path, for directing light from the object along both a first optical path and a second optical path;

(d) a first collection lens disposed in the first optical path, the first collection lens having a first focal point;

(e) a first optical grating disposed in the first optical path between the first collection lens and the first focal point, the first optical grating modulating the light from the object to produce first modulated light having a modulation frequency proportional to a velocity of the object passing through the field of view;

(f) a first light sensitive detector on which the first modulated light is incident, the first light sensitive detector producing a first electrical signal responsive to the first modulated light;

(g) a second collection lens disposed in the second optical path, the second collection lens having a second focal point; such that light traveling from the primary optical element to the second focal point travels substantially the same distance as light traveling from the primary optical element to the first focal point;

(h) a second optical grating disposed in the second optical path, the second optical grating modulating light from the object to produce second modulated light having a modulation frequency proportional to the velocity of the object passing through the field of view, the second optical grating being disposed such that:

(1) light traveling from the primary optical element to the second optical grating travels farther than light traveling from the primary optical element to the second focal point; and (2) a distance separating the first optical grating from the first focal point is substantially the same as a distance separating the second optical grating from the second focal point;

(i) a second light sensitive detector on which the second modulated light is incident, the second light sensitive detector producing a second electrical signal responsive to the second modulated light; and (j) a controller logically coupled to the prime mover, the first light sensitive detector, and the second light sensitive detector, the controller being configured to iteratively:

(1) process the first electrical signal and the second electrical signal to determine a direction in which the primary optical element should be moved to more closely position a focal point of the primary optical element on the object; and (2) activate the prime mover to move the primary optical element a predefined distance in the direction determined.

14. The imaging system of claim 13, wherein each element in the first optical path is matched to a corresponding element in the second optical path.

15. The imaging system of claim 13, wherein the controller comprises at least one of an application specific integrated circuit and a programmable computing device.

16. The imaging system of claim 13, wherein the controller processes at least one of the first electrical signal and the second electrical signal to determine an indication of the velocity of the object relative to the imaging system.

17. The imaging system of claim 13, wherein the controller processes the first electrical signal and the second electrical signal to determine an indication of the velocity of the object relative to the imaging system by:

(a) determining a focus signal measurement for the first electrical signal;

(b) determining a focus signal measurement for the second electrical signal;

(c) determining the velocity of the object relative to the imaging system based on the first electrical signal;

(d) determining the velocity of the object relative to the imaging system based on the second electrical signal; and (e) determining the velocity of the object relative to the imaging system based on the focus signal measurement for the first electrical signal, the focus signal measurement for the second electrical signal, the velocity of an object relative to the imaging system as determined based on the first electrical signal, and the velocity of the object relative to the imaging system as determined based on the second electrical signal.

18. The imaging system of claim 16, further comprising at least one additional light sensitive detector disposed to receive the light traveling along the collection path that is not modulated by either the first optical grating and the second optical grating, and which is employed to determine a characteristic of the object, said splitter means further splitting light traveling along the collection path into light traveling along a third optical path that is received by said at least one additional light sensitive detector.

19. The imaging system of claim 18, wherein said least one additional light sensitive detector comprise a time delay integration (TDI) detector logically coupled to the controller, and wherein the controller uses the indication of the velocity of the object to synchronize the TDI detector with a relative motion of the object.

20. A method for automatically focusing an imaging system on an object in a field of view while there is relative movement between the object and the imaging system, the method comprising the steps of:

(a) collecting light from the object;

(b) modulating light collected from the object to produce first modulated light having a modulation frequency that is a function of a velocity of the object;

(c) producing a first signal corresponding to an intensity of the first modulated light;

(d) modulating light collected from the object to produce second modulated light having a modulation frequency that is a function of the velocity of the object, wherein light travels from the object a greater distance before being modulated to produce the first modulated light than light traveling from the object before being modulated to produce the second modulated light;

(e) producing a second signal corresponding to an intensity of the second modulated light;

(f) processing the first signal and the second signal to determine a direction in which a focus on the object should be adjusted to improve the focus on the object; and (g) adjusting the focus on the object in the direction determined.

21. The method of claim 20, further comprising the step of repeating steps (a)–(g) to further improve the focus on the object.

22. The method of claim 20, further comprising the step of manipulating at least one of the first signal and the second signal to determine an indication of the velocity of the object relative to the imaging system.

23. The method of claim 20, further comprising the steps of:
   (a) determining a focus signal measurement for the first signal;
   (b) determining a focus signal measurement for the second signal;
   (c) determining the velocity of the object relative to the imaging system based on the first signal;
   (d) determining the velocity of the object relative to the imaging system based on the second signal;
   (e) determining the velocity of the object relative to the imaging system based on the focus signal measurement for the first signal, the focus signal measurement for the second signal, the velocity of the object relative to the imaging system based on the first signal, and the velocity of the object relative to the imaging system based on the second signal.

24. The method of claim 22, further comprising the step of using the indication of the velocity of the object to synchronize a time delay integration detector to the relative motion of the object.

25. A method for automatically focusing an imaging system on an object in a field of view while there is relative movement between the object and the imaging system, and determining at least one non velocity characteristic of the object, comprising the steps of:
   (a) collecting light from the object;
   (b) modulating light collected from the object to produce first modulated light having a modulation frequency that is a function of the velocity of the object;
   (c) producing a first signal corresponding to an intensity of the first modulated light;
   (d) modulating light collected from the object to produce second modulated light having a modulation frequency that is a function of the velocity of the object, wherein light travels from the object a greater distance before being modulated to produce the first modulated light than light traveling from the object before being modulated to produce the second modulated light;
   (e) producing a second signal corresponding to an intensity of the second modulated light;
   (f) processing the first signal and the second signal to determine a direction in which a focus on the object should be adjusted to improve the focus on the object; and
   (g) adjusting the focus on the object in the direction determined;
   (h) dispersing light collected from the object that is not modulated to produce either first modulated light or second modulated light;
   (i) directing the dispersed light onto a detector disposed to receive the dispersed light; and
   (j) analyzing an output signal from the detector to determine the at least one non velocity characteristic of the object.

26. The method of claim 25, further comprising the step of repeating steps (a)–(g) to further improve the focus on the object.

27. The method of claim 25, further comprising the step of manipulating at least one of the first signal and the second signal to determine an indication of the velocity of the object relative to the imaging system.

28. The method of claim 25, further comprising the steps of:
   (a) determining a focus signal measurement for the first signal;
   (b) determining a focus signal measurement for the second signal;
   (c) determining the velocity of the object relative to the imaging system based on the first signal;
   (d) determining the velocity of the object relative to the imaging system based on the second signal; and
   (e) determining the velocity of the object relative to the imaging system based on the focus signal measurement for the first signal, the focus signal measurement for the second signal, the velocity of the object relative to the imaging system based on the first signal, and the velocity of the object relative to the imaging system based on the second signal.

29. The method of claim 27, wherein the detector is a time delay integration (TDI) detector, and further comprising the step of using the indication of the velocity of the object to synchronize the (TDI) to the relative motion of the object.

* * * * *